United States Patent
Salmanzadeh et al.

(10) Patent No.: US 11,946,038 B1
(45) Date of Patent: Apr. 2, 2024

(54) METHODS AND SYSTEMS INCLUDING FLOW AND MAGNETIC MODULES

(71) Applicant: 10X Genomics, Inc., Pleasanton, CA (US)

(72) Inventors: Alireza Salmanzadeh, Pleasanton, CA (US); Dagmar Walter, San Francisco, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

(21) Appl. No.: 17/332,371

(22) Filed: May 27, 2021

Related U.S. Application Data

(60) Provisional application No. 63/031,913, filed on May 29, 2020.

(51) Int. Cl.
*C12N 15/10* (2006.01)
*B03C 1/28* (2006.01)

(52) U.S. Cl.
CPC ............ *C12N 15/1013* (2013.01); *B03C 1/28* (2013.01); *B03C 2201/18* (2013.01); *B03C 2201/26* (2013.01)

(58) Field of Classification Search
CPC ............... C12N 15/10; C12N 15/1003; C12N 15/1013; B03C 2201/00; B03C 2201/18; B03C 2201/20; B03C 2201/22; B03C 1/28; B03C 1/286
See application file for complete search history.

(56) References Cited

U.S. PATENT DOCUMENTS

| | | |
|---|---|---|
| 5,658,548 A | 8/1997 | Padhye et al. |
| 5,705,628 A | 1/1998 | Hawkins |
| 5,897,783 A | 4/1999 | Howe et al. |
| 6,133,436 A | 10/2000 | Koster et al. |
| 7,718,421 B2 | 5/2010 | Chen et al. |
| 9,182,395 B2 | 11/2015 | Tajima |
| 9,347,056 B2 | 5/2016 | Saito et al. |
| 9,839,911 B2 | 12/2017 | Weitz et al. |
| 9,975,122 B2 | 5/2018 | Masquelier et al. |
| 10,011,872 B1 | 7/2018 | Belgrader et al. |
| 10,245,587 B2 | 4/2019 | Masquelier et al. |
| 10,323,278 B2 | 6/2019 | Belgrader et al. |
| 10,544,413 B2 | 1/2020 | Bharadwaj et al. |
| 10,697,000 B2 | 6/2020 | Belgrader et al. |
| 10,976,225 B2 | 4/2021 | Rackus et al. |
| 11,135,584 B2 | 10/2021 | Masquelier et al. |
| 11,660,601 B2 | 5/2023 | Bharadwaj et al. |

(Continued)

FOREIGN PATENT DOCUMENTS

| | | |
|---|---|---|
| EP | 1944368 A1 | 7/2008 |
| TW | I492791 B | 7/2015 |

(Continued)

OTHER PUBLICATIONS

U.S. Appl. No. 17/242,802, Salmanzadeh.

(Continued)

*Primary Examiner* — Ryan B Huang
(74) *Attorney, Agent, or Firm* — Clark & Elbing LLP

(57) ABSTRACT

Systems, and their methods of use, for sorting or separating magnetic particles are provided. A system having a magnetic module with features that mate with voids in a flow module exerts a magnetic field on magnetic particles to separate particles.

19 Claims, 5 Drawing Sheets

(56) References Cited

U.S. PATENT DOCUMENTS

| | | |
|---|---|---|
| 11,701,668 B1 | 7/2023 | Salmanzadeh |
| 2003/0027203 A1 | 2/2003 | Fields |
| 2004/0040851 A1 | 3/2004 | Karger et al. |
| 2004/0214175 A9 | 10/2004 | McKernan et al. |
| 2005/0013741 A1 | 1/2005 | a' Brassard |
| 2005/0172476 A1 | 8/2005 | Stone et al. |
| 2006/0094108 A1 | 5/2006 | Yoder et al. |
| 2006/0163385 A1 | 7/2006 | Link et al. |
| 2007/0003422 A1 | 1/2007 | Yildirim et al. |
| 2007/0077604 A1 | 4/2007 | Wyatt et al. |
| 2012/0045828 A1* | 2/2012 | Davis .............. B03C 1/01 435/308.1 |
| 2012/0190037 A1 | 7/2012 | Durin et al. |
| 2012/0261348 A1 | 10/2012 | Roh et al. |
| 2014/0235506 A1 | 8/2014 | Hindson et al. |
| 2015/0031037 A1 | 1/2015 | Li et al. |
| 2015/0361418 A1 | 12/2015 | Reed |
| 2016/0298107 A1 | 10/2016 | O'Farrell et al. |
| 2019/0329245 A1 | 10/2019 | Masquelier et al. |
| 2020/0115703 A1 | 4/2020 | Bharadwaj et al. |
| 2020/0256863 A1 | 8/2020 | Toei et al. |
| 2021/0032678 A1 | 2/2021 | Belgrader et al. |
| 2021/0187515 A1 | 6/2021 | Alimsijah et al. |
| 2021/0293693 A1 | 9/2021 | Bharadwaj et al. |
| 2022/0097045 A1 | 3/2022 | Masquelier et al. |
| 2023/0271187 A1 | 8/2023 | Bharadwaj et al. |

FOREIGN PATENT DOCUMENTS

| | | |
|---|---|---|
| WO | WO-9716835 A1 | 5/1997 |
| WO | WO-2006/071770 A2 | 7/2006 |
| WO | WO-2009/005680 A1 | 1/2009 |
| WO | WO-2009/006409 A2 | 1/2009 |
| WO | WO-2012/019765 A1 | 2/2012 |
| WO | WO-2014/182835 A1 | 11/2014 |
| WO | WO-2016/137973 A1 | 9/2016 |
| WO | WO-2018/009766 A1 | 1/2018 |
| WO | WO-2018/213643 A1 | 11/2018 |
| WO | WO-2019/088106 A1 | 5/2019 |
| WO | WO-2019/157529 A1 | 8/2019 |
| WO | WO-2020/123657 A2 | 6/2020 |
| WO | WO-2021/102043 A1 | 5/2021 |

OTHER PUBLICATIONS

U.S. Appl. No. 17/314,756, Salmanzadeh.
U.S. Appl. No. 17/332,371, Salmanzadeh et al.
U.S. Appl. No. 17/338,215, Salmanzadeh et al.
U.S. Appl. No. 17/851,416, Bharadwaj et al.
U.S. Appl. No. 17/742,793, Alimsijah et al.
U.S. Appl. No. 17/587,861, Shah.
Song et al., "Reactions in Droplets in Microfluidic Channels," available in PMC Jan. 10, 2007, published in final edited form as: Angew Chem Int Ed Engl. 45(44):7336-56 (2006) (Nov. 13, 2006) (58 pages).
Mazutis et al., "Single-cell analysis and sorting using droplet-based microfluidics," available in PMC Aug. 11, 2014, published in final edited form as: Nat Protoc. 8(5):870-91 (2013) (48 pages).
Lennon et al., "A scalable, fully automated process for construction of sequence-ready barcoded libraries for 454," Genome Biol. 11(2):R15 (2010) (9 pages).
"Dynal MPC™-S," Invitrogen, <https://www.veritastk.co.jp/products/pdf/120%2020D.Dynal_MPC-S(rev005).pdf>, dated Oct. 13, 2008, retrieved on Jul. 9, 2019 (1 page).
Myklatun et al., "Microfluidic sorting of intrinsically magnetic cells under visual control," Sci Rep. 7(1):6942 (Jul. 2017) (8 pages).
Ge et al., "Magnetic matrices used in high gradient magnetic separation (HGMS): A review," Results in Physics. 7:4278-4286 (Oct. 2017).

* cited by examiner

METHODS AND SYSTEMS INCLUDING FLOW AND MAGNETIC MODULES

BACKGROUND OF THE INVENTION

Many biomedical applications rely on high-throughput assays of samples combined with one or more reagents in droplets or particles. For example, in both research and clinical applications, high-throughput genetic tests using target-specific reagents may provide information about samples in drug discovery, biomarker discovery, and clinical diagnostics, among others. Many of these applications, following the formation of a droplet or particle, rely on the presence of a reagent or material within the droplet or particle. For example, some of these applications rely on the presence of a cell or nucleus or particulate component thereof. However, before droplet formation, precise sample preparation may be required. Other devices and methods for sorting may disturb a particle and alter its characteristics (e.g., gene expression, activation, or viability). Therefore, improved devices and methods for purification would be beneficial.

SUMMARY OF THE INVENTION

In one aspect, the invention features a system for magnetic separation. The system includes a flow module with a sorting region having an inlet and an outlet and includes a plurality of voids around which particles and fluid can flow. The system further includes a magnetic module with a plurality of magnetic features that mate with the plurality of voids. The magnetic and flow modules may be separable.

In some embodiments, the magnetic features have an average width of from about 1 μm to about 10 mm. The length, width, and height may be, independently, from about 1 μm to about 10 mm (e.g., about 1 μm, 2 μm, 3 μm, 4 μm, 5 μm, 6 μm, 7 μm, 8 μm, 9 μm, or 10 μm, e.g., from about 10 μm to about 100 μm, e.g., about 20 μm, 30 μm, 40 μm, 50 μm, 60 μm, 70 μm, 80 μm, 90 μm, or 100 μm, e.g., from about 100 μm to about 1,000 μm, e.g., about 200 μm, 300 μm, 400 μm, 500 μm, 600 μm, 700 μm, 800 μm, 900 μm, or 1,000 μm, e.g., from about 1 mm to about 10 mm, e.g., about 2 mm, 3 mm, 4 mm, 5 mm, 6 mm, 7 mm, 8 mm, 9 mm, or 10 mm).

In some embodiments, the magnetic features are spaced apart from each other at an average distance of from about 1 nm to about 100 μm (e.g., from about 10 nm to about 1 μm, from about 5 μm to about 10 μm, or from about 10 μm to about 50 μm).

In some embodiments, the flow module further includes a collection region in fluid communication with the outlet.

In some embodiments, the voids include, i.e., are bounded by, a wall having a thickness of 10 μm to about 10 mm that separates the magnetic features from particles and fluid in the sorting region.

In some embodiments, the system further includes a magnet operatively coupled to the features, wherein the magnetic features are magnetizable.

In some embodiments, the magnetic features include a ferromagnetic or paramagnetic material.

In some embodiments, the flow module is manufactured from plastic, silicone, glass, or silicon.

In some embodiments, the voids have a cylindrical or polygonal cross-section, e.g., perpendicular to the direction of flow in the flow module. For example, the cross-section is triangular or rectangular.

In another aspect, the invention features a method for magnetic separation. The method includes providing a system of the invention and a sample with magnetic particles suspended in a liquid and allowing the sample to enter the sorting region. The magnetic particles may be immobilized adjacent the voids in the sorting region.

In some embodiments, the method further includes washing the magnetic particles.

In some embodiments, the method further includes eluting the magnetic particles. Eluting the magnetic particles may include removing the magnetic module from the flow module. Eluting the magnetic particles may include resuspending the magnetic particles in a second liquid.

In some embodiments, the magnetic particles are attached to a biological particle or a macromolecular constituent thereof. The biological particle may be a cell.

Definitions

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "about," as used herein, refers to ±10% of a recited value.

The terms "adaptor(s)," "adapter(s)," and "tag(s)" may be used synonymously. An adaptor or tag can be coupled to a polynucleotide sequence to be "tagged" by any approach including ligation, hybridization, or other approaches.

The term "barcode," as used herein, generally refers to a label, or identifier, that conveys or is capable of conveying information about an analyte. A barcode can be part of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads in real time.

The term "bead," as used herein, generally refers to a particle that is not a biological particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

The term "biological particle," as used herein, generally refers to a discrete biological system derived from a biological sample. The biological particle may be a virus. The biological particle may be a cell or derivative of a cell. The biological particle may be an organelle from a cell. Examples of an organelle from a cell include, without limitation, a nucleus, endoplasmic reticulum, a ribosome, a Golgi apparatus, an endoplasmic reticulum, a chloroplast, an endocytic vesicle, an exocytic vesicle, a vacuole, and a lysosome. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be a constituent of a cell. The biological particle may be or may include DNA, RNA, organelles, proteins, or any combination thereof. The biological particle may be or may include a matrix (e.g., a gel or polymer matrix) comprising a cell or one or more constituents from a cell (e.g., cell bead), such as DNA, RNA, organelles, proteins, or any combination thereof, from the cell. The biological particle may be obtained from a tissue of a subject. The biological particle may be a hardened cell. Such hardened cell may or may not include a cell wall or cell membrane. The biological particle may include one or more constituents of a cell, but may not include other constituents of the cell. An example of such constituents is a nucleus or another organelle of a cell. A cell may be a live cell. The live cell may be capable of being cultured, for example, being cultured when enclosed in a gel or polymer matrix, or cultured when comprising a gel or polymer matrix.

The term "center axis," as used herein refers to the axis down the length of the middle of a channel in the direction of fluid flow.

The term "coupled to a magnet," as used herein, refers to components that are connected to induce magnetic dipole moments in at least one of the components. A magnetic fluid coupled to a magnet results in the generation of a magnetic gradient.

The term "fluidically connected," as used herein, refers to a direct connection between at least two device elements, e.g., a channel, reservoir, etc., that allows for fluid to move between such device elements without passing through an intervening element.

The term "genome," as used herein, generally refers to genomic information from a subject, which may be, for example, at least a portion or an entirety of a subject's hereditary information. A genome can be encoded either in DNA or in RNA. A genome can comprise coding regions that code for proteins as well as non-coding regions. A genome can include the sequence of all chromosomes together in an organism. For example, the human genome has a total of 46 chromosomes. The sequence of all of these together may constitute a human genome.

The term "in fluid communication with", as used herein, refers to a connection between at least two device elements, e.g., a channel, reservoir, etc., that allows for fluid to move between such device elements with or without passing through one or more intervening device elements.

The term "macromolecular constituent," as used herein, generally refers to a macromolecule contained within or from a biological particle. The macromolecular constituent may comprise a nucleic acid. In some cases, the biological particle may be a macromolecule. The macromolecular constituent may comprise DNA or a DNA molecule. The macromolecular constituent may comprise RNA or an RNA molecule. The RNA may be coding or non-coding. The RNA may be messenger RNA (mRNA), ribosomal RNA (rRNA) or transfer RNA (tRNA), for example. The RNA may be a transcript. The RNA molecule may be (i) a clustered regularly interspaced short palindromic (CRISPR) RNA molecule (crRNA) or (ii) a single guide RNA (sgRNA) molecule. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide or a protein. The polypeptide or protein may be an extracellular or an intracellular polypeptide or protein. The macromolecular constituent may also comprise a metabolite. These and other suitable macromolecular constituents (also referred to as analytes) will be appreciated by those skilled in the art (see U.S. Pat. Nos. 10,011,872 and 10,323,278, and PCT Publication No. WO 2019/157529, each of which is incorporated herein by reference in its entirety).

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise an oligonucleotide or polypeptide sequence. The molecular tag may comprise a DNA aptamer. The molecular tag may be or comprise a primer. The molecular tag may be or comprise a protein. The molecular tag may comprise a polypeptide. The molecular tag may be a barcode.

The term "oil," as used herein, generally refers to a liquid that is not miscible with water. An oil may have a density higher or lower than water and/or a viscosity higher or lower than water.

The terms "operative contact" and "operatively connected," as used herein, generally refers to a functional relationship between components. A magnetic feature and a flow module are separated by a wall that allows a magnetic field from the magnetic feature to interact with particles, e.g., magnetic particles, on the other side of the wall in the flow module. The magnetic feature may or may not be in conformal physical contact with the wall of the flow module.

The term "particulate component of a cell" refers to a discrete biological system derived from a cell or fragment thereof and having at least one dimension of 0.01 µm (e.g., at least 0.01 µm, at least 0.1 µm, at least 1 µm, at least 10 µm, or at least 100 µm). A particulate component of a cell may be, for example, an organelle, such as a nucleus, an exosome, a liposome, an endoplasmic reticulum (e.g., rough or smooth), a ribosome, a Golgi apparatus, a chloroplast, an endocytic vesicle, an exocytic vesicle, a vacuole, a lysosome, or a mitochondrion.

The term "sample," as used herein, generally refers to a biological sample of a subject. The biological sample may be a nucleic acid sample or protein sample. The biological sample may be derived from another sample. The sample may be a tissue sample, such as a biopsy, core biopsy, needle aspirate, or fine needle aspirate. The sample may be a liquid sample, such as a blood sample, urine sample, or saliva sample. The sample may be a skin sample. The sample may be a cheek swap. The sample may be a plasma or serum sample. The sample may include a biological particle, e.g., a cell, a nucleus, or virus, or a population thereof, or it may alternatively be free of biological particles. A cell-free sample may include polynucleotides. Polynucleotides may be isolated from a bodily sample that may be selected from the group consisting of blood, plasma, serum, urine, saliva, mucosal excretions, sputum, stool and tears.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by ILLUMINA®, Pacific Biosciences (PACBIO®), Oxford NANOPORE®, or Life Technologies (ION TORRENT®). Alternatively or in addition, sequencing may be performed using nucleic acid amplification, polymerase chain reaction (PCR) (e.g., digital PCR, quantitative PCR, or real time PCR), or isothermal amplification. Such devices may provide a plurality of raw genetic data corresponding to the genetic information of a subject (e.g., human), as generated by the device from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "sorter," as used herein, generally refers to a mechanism that causes movement of one or more droplets or particles into one of two or more partitions (e.g., channels or regions), e.g., in a collection region. A sorter may be active or passive. In active sorting, actuation of the sorter moves a droplet to a partition. In passive sorting, droplets are moved to a partition based on an intrinsic property, e.g., mass, buoyancy, size, magnetic properties, or electrical properties.

The term "subject," as used herein, generally refers to an animal, such as a mammal (e.g., human) or avian (e.g., bird), or other organism, such as a plant. The subject can be a vertebrate, a mammal, a mouse, a primate, a simian or a human. Animals may include, but are not limited to, farm animals, sport animals, and pets. A subject can be a healthy or asymptomatic individual, an individual that has or is suspected of having a disease (e.g., cancer) or a predisposition to the disease, or an individual that is in need of therapy or suspected of needing therapy. A subject can be a patient.

The term "substantially stationary", as used herein with respect to droplet or particle formation, generally refers to a state when motion of formed droplets or particles in the continuous phase is passive, e.g., resulting from the difference in density between the dispersed phase and the continuous phase.

DETAILED DESCRIPTION OF THE INVENTION

Figure 1:
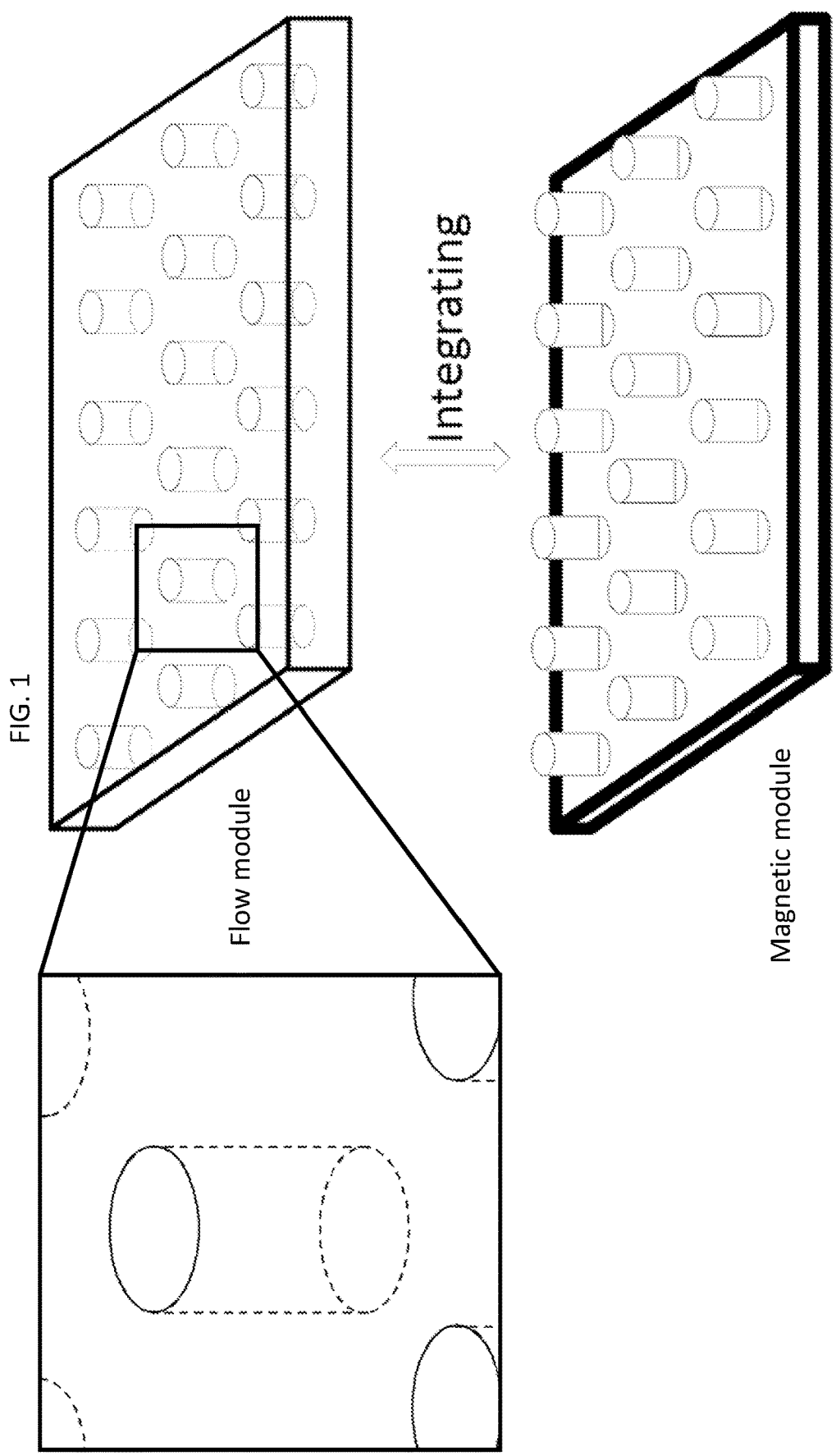
FIG. 1 is a schematic drawing of a system with a flow module (top) and a magnetic module (bottom).

The invention provides systems for magnetic separation of particles and methods of their use. The systems may be used to sort particles of a desired property, e.g., for genetic sequencing.

The systems and methods described herein allow for the separation of magnetic particles. The magnetic particles may be released from a droplet or larger particle or may be a label present on another particle (e.g., cell, a nucleus, a macromolecular constituent of a cell, a gel bead, or a combination thereof). The magnetic particles may be used to purify particles or molecules attached thereto for incorporation into droplets or other, larger particles (e.g., gels). The magnetic separation is performed by a magnetic separation system that includes a flow module with an inlet and an outlet and plurality of voids and a magnetic module with a plurality of magnetic features that mate with the voids. The flow module and the magnetic module are separable. Advantages of the systems and methods described herein are that the magnetic separation devices provide a quick and gentle separation that minimizes damage to the magnetic particles or the components attached thereto, e.g., cell disruption or changes in gene expression, which may increase viability of the component being separated (e.g., a cell, a nucleus, or a macromolecular constituent thereof, e.g., organelle), e.g., relative to other devices, systems, and methods.

System for Magnetic Separation

A system for magnetic separation includes a separable flow module and magnetic module. The flow module includes an inlet and an outlet with a plurality of voids around which a sample (e.g., fluid and particles) can flow. The system also includes a magnetic module with a plurality of magnetic features that mate with the plurality of voids. Each component is separable from each other to allow for facile removal of the magnetic field from the flow module. By positioning the magnetic module and the magnetic material therein outside of a sorting region in the flow module, the magnetic module and its features do not directly contact the magnetic particles or anything bound thereto. Therefore, when the magnetic particles are attached to, e.g., a biological particle or macromolecular constituent (e.g., a cell, a nucleus, or macromolecular constituent thereof), the magnetic particles do not become entrapped, e.g., as may occur in a column packed with magnetic beads or magnetic sources, and the magnetic particles may be more easily released. Additionally, this arrangement allows the magnetic module to be reused with multiple samples as the magnetic module does not become contaminated between uses and, therefore, does not require washing or sterilization for subsequent use. Finally, other devices and systems for magnetic separation that do not employ a design as described herein require fabrication with magnetic material within the device, which makes the fabrication process expensive and less scalable. The components of the system are described in more detail below. The magnetic features and void may mate with each other on a one to one basis, or the number of voids may exceed the number of magnetic features. For example, the flow module may have a void pattern that is usable with magnetic modules that have different patterns of features (that nonetheless mate with the voids). The magnetic features may also mate conformally with the walls bounding the voids, or there may be spacing between the walls and the features. Lubricants, magnetic or non-magnetic, may also be employed to facilitate mating and unmating of the modules.

Magnetic Module

A magnetic module of a system as described herein includes a plurality of magnetic features (e.g., pillars) containing a magnetic material. The features may be any structure, e.g., that protrudes from the base of the magnetic module. The magnetic features may be any size and shape provided that they can mate with the flow module and provide a magnetic field in the path of fluid flow. For example, the magnetic features may be cylindrical, rectangular, triangular, or have any suitable polygonal shape (e.g., a cross-section of the feature is a triangle, rectangle, pentagon, hexagon, or the like).

The magnetic module may contain different sized or shaped magnetic features, or the magnetic features may be substantially identical throughout. Each dimension of each feature may be, e.g., from about 1 µm to about 10 mm. For example, the length, width, and height may be, independently, e.g., from about 1 µm to about 10 mm (e.g., about 1 µm, 2 µm, 3 µm, 4 µm, 5 µm, 6 µm, 7 µm, 8 µm, 9 µm, or 10 µm, e.g., from about 10 µm to about 100 µm, e.g., about 20 µm, 30 µm, 40 µm, 50 µm, 60 µm, 70 µm, 80 µm, 90 µm, or 100 µm, e.g., from about 100 µm to about 1,000 µm, e.g., about 200 µm, 300 µm, 400 µm, 500 µm, 600 µm, 700 µm, 800 µm, 900 µm, or 1,000 µm, e.g., from about 1 mm to about 10 mm, e.g., about 2 mm, 3 mm, 4 mm, 5 mm, 6 mm, 7 mm, 8 mm, 9 mm, or 10 mm).

The magnetic features may be arranged, e.g., in a grid pattern. The arrangement of the magnetic features may be determined, e.g., empirically, based on the size of the particle (e.g., a cell or macromolecular constituent thereof) being sorted or separated. The magnetic features may be spaced apart from one another at a predetermined distance of about 1 nm to about 10 mm (e.g., from about 10 nm to about 100 µm, e.g., from about 10 nm to about 1 µm, from about 5 µm to about 10 µm, or from about 10 µm to about 50 µm). For example, the magnetic features may be spaced at a predetermined distance of from about 1 nm to about 10 nm, e.g., about 1 nm, 2 nm, 3 nm, 4 nm, 5 nm, 6 nm, 7 nm, 8 nm, 9 nm, or 10 nm, e.g., from about 10 nm to about 100 nm, e.g., about 20 nm, 30 nm, 40 nm, 50 nm, 60 nm, 70 nm, 80 nm, 90 nm, or 100 nm, e.g., from about 100 nm to about 1,000 nm, e.g., about 1 µm, 2 µm, 3 µm, 4 µm, 5 µm, 6 µm, 7 µm, 8 µm, 9 µm, or 10 µm, e.g., from about 10 µm to about 100 µm, e.g., 20 µm, 30 µm, 40 µm, 50 µm, 60 µm, 70 µm, 80 µm, 90 µm, or 100 µm, e.g., from about 100 µm to about 1,000 µm, e.g., about 200 µm, 300 µm, 400 µm, 500 µm, 600 µm, 700 µm, 800 µm, 900 µm, or 1,000 µm, e.g., from about 1 mm to about 10 mm, e.g., about 2 mm, 3 mm, 4 mm, 5 mm, 6 mm, 7 mm, 8 mm, 9 mm, or 10 mm. In one embodiment, the magnetic features are spaced apart, e.g., from about 5 µm to about 10 µm, to sort or separate smaller cells, such as blood cells (e.g., erythrocytes). In one embodiment, the magnetic features are spaced, e.g., from about 10 µm to about 50 µm, e.g., to sort or separate larger cells. If a nucleic acid (e.g., DNA or RNA) is being sorted or separated, the spacing may be limited, e.g., by the size of the magnetic particles (e.g., «1 µm, e.g., about 1 nm).

The magnetic features may be positioned in one particular area of the magnetic module, so they are disposed, e.g., on one side of the sorting region. This configuration allows the features to attract the magnetic particles to one side of the flow module, so they are enriched relative to unlabeled particles. The flow module may have multiple outlets to separate a portion enriched in magnetic particles from a portion not enriched.

The magnetic module may contain at least one magnetic feature. The magnetic module may contain a plurality of features. For example, the magnetic module may contain at least 2, 3, 4, 5, 6, 7, 8, 9, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, or more magnetic features.

The magnetic features may contain one or more, e.g., a plurality of (e.g., at least 2, 3, 4, 5, 6, 7, 8, 9, 10, or more) sharp features. The corner of the sharp feature may be, for example, pointed, rounded, or chamfered. For example, the sharp feature may have a corner radius of less than about 10 mm (e.g., less than about 9 mm, 8 mm, 7 mm, 6 mm, 5 mm, 4 mm, 3 mm, 2 mm, or 1 mm, e.g., less than about 990 µm, 980 µm, 970 µm, 960 µm, 950 µm, 940 µm, 930 µm, 920 µm, 910 µm, or 900 µm, e.g., less than about 800 µm, 700 µm, 600 µm, 500 µm, 400 µm, 300 µm, 200 µm, or 100 µm, e.g., less than about 90 µm, 80 µm, 70 µm, 60 µm, or 50 µm, e.g., less than about 45 µm, 40 µm, 35 µm, 30 µm, 25 µm, 20 µm, 15 µm, or 10 µm, e.g., less than about 9 µm, 8 µm, 7 µm, 6 µm, 5 µm, 4 µm, 3 µm, 2 µm or 1 µm, e.g., from about 10 mm to about 1 µm, from about 1 mm to about 1 µm, from about 500 µm to about 1 µm, from about 100 µm to about 1 µm, from about 10 µm to about 1 µm, from about 1 mm to about 10 µm, from about 100 µm to about 10 µm, from about 50 µm to about 10 µm, from about 10 µm to about 1 µm, from about 10 mm to about 1 mm, from about 10 mm to about 5 mm, from about 5 mm to about 500 µm, from about 1 mm to about 500 µm, from about 1 mm to about 10 µm). For example, the feature may have a corner radius of less than about 1 mm. The feature may produce a magnetic gradient of at least about 10 T/m (e.g., at least about 20 T/m, 30 T/m, 40 T/m, 50 T/m, 60 T/m, 70 T/m, 80 T/m, 90 T/m, or 100 T/m, e.g., at least about 200 T/m, 300 T/m, 400 T/m, 500 T/m, 600 T/m, 700 T/m, 800 T/m, 900 T/m, or 1,000 T/m, e.g., at least about 2,000 T/m, 3,000 T/m, 4,000 T/m, 5,000 T/m, 6,000 T/m, 7,000 T/m, 8,000 T/m, 9,000 T/m, 10,000 T/m, e.g., at least about 20,000 T/m, 30,000 T/m, 40,000 T/m, 50,000 T/m, 60,000 T/m, 70,000 T/m, 80,000 T/m, 90,000 T/m, or 100,000 T/m, e.g., at least about 200,000 T/m, 300,000 T/m, 400,000 T/m, 500,000 T/m, 600,000 T/m, 700,000 T/m, 800,000 T/m, 900,000 T/m, or 1,000,000 T/m, e.g., at least about 2,000,000 T/m, 3,000,000 T/m, 4,000,000 T/m, 5,000,000 T/m, 6,000,000 T/m, 7,000,000 T/m, 8,000,000 T/m, 9,000,000 T/m, or 10,000,000, e.g., at least about 100,000,000 T/m, 200,000,000 T/m, 300,000,000 T/m, 400,000,000 T/m, 500,000,000 T/m, 600,000,000 T/m, 700,000,000 T/m, 800,000,000 T/m, 900,000,000 T/m, or 1,000,000,000, or greater, e.g., from about 10 T/m to about 1,000,000,000 T/m, from about 100 T/m to about 1,000,000,000 T/m, from about 1,000 T/m to about 1,000,000,000 T/m, from about 10,000 T/m to about 10,000,000,000 T/m, from about 10,000,000 T/m to about 1,000,000,000 T/m, from about 100,000 T/m, to about 100,000,000 T/m, from about 100,000 T/m to about 100,000,000 T/m, from about 100,000 T/m to about 10,000,000 T/m, from about 10,000,000 T/m to about 100,000,000 T/m. For example, the feature may produce a magnetic gradient of at least about 100,000 T/m.

The sharp feature of the magnetic feature may produce a magnetic field gradient, e.g., that is stronger compared to a feature without such a feature, e.g., having a corner radius of less than 10 mm, e.g., less than 1 mm.

One of skill in the art would appreciate that the values above, such as the corner radius of the sharp feature or the magnetic gradient, may be determined empirically. For example, the magnetic gradient may depend on factors, such as the size of magnetic particles (e.g., that are being separated, e.g., that are attached to a biological particle or macromolecular constituent thereof), the number of magnetic particles attached to each biological particle or macromolecular constituent thereof, the size and material of the magnetic particles, the tolerance of fabricating the magnets, the thickness of the barrier, the tightness of fit between the magnetic channel, the barrier, and the sample channel, and, if present, the sharpness (angle) of the feature.

The magnetic features may be or include, e.g., any magnetic material, such as a ferromagnetic or paramagnetic material. The magnetic features may contain a magnetic fluid, e.g., any fluidic component containing, e.g., a liquid, that becomes magnetized in the presence of a magnetic field. The magnetic fluid may be or include a ferrofluid. The ferrofluid may include magnetite $Fe_3O_4$ nanoparticles, maghemite $Fe_2O_3$, or a combination thereof. The magnetic fluid may include a paramagnetic salt. The magnetic salt may include $MnCl_2$, gado-diethylenetriaminepentaacetic acid (Gd-DTPA), or a combination thereof.

In some embodiments, the system further includes a magnet that is operatively coupled to the magnetic features of the magnetic module. For example, the magnetic features may be magnetizable or may contain a magnetizable material. The magnet can be any magnet that exerts force on magnetic particles. A magnetic field may be provided by one or more (e.g., a plurality of) magnets, such as permanent magnet or an electromagnet. The magnet may be positioned on, within, or near the magnetic features such that its magnetic gradient is coupled to the magnetic features. The magnet may be part of the magnetic module, e.g., integrated within the module. Alternatively, the magnet may be removably attached to the magnetic module, or provided as a separate component (e.g., as part of the system). The system may include a plurality (e.g., 2, 3, 4, 5, 6, 7, 8, 9, 10, or more) of magnets. The magnets may be positioned such that each magnet is coupled to a magnetic feature, e.g., a plurality of magnets each coupled to a separate magnetic feature or a plurality of magnets each coupled to the same magnetic feature. In some embodiments, one magnet is coupled to a plurality of magnetic features.

Flow Module

The systems described herein include a flow module having an inlet and an outlet and a plurality of voids around which a sample can flow. The plurality of voids may be any size and shape such they are configured to mate with the magnetic features of the magnetic module. For example, the voids may be cylindrical, rectangular, triangular, or have any suitable polygonal shape (e.g., a cross-section of the feature is a triangle, rectangle, pentagon, hexagon, and the like).

The flow module may contain different sized or shaped voids, or the voids may be substantially identical throughout. Each dimension of each void may be, e.g., from about 1 μm to about 10 mm. For example, the length, width, and height may be, independently, e.g., from about 1 μm to about 10 mm (e.g., about 1 μm, 2 μm, 3 μm, 4 μm, 5 μm, 6 μm, 7 μm, 8 μm, 9 μm, or 10 μm, e.g., from about 10 μm to about 100 μm, e.g., about 20 μm, 30 μm, 40 μm, 50 μm, 60 μm, 70 μm, 80 μm, 90 μm, or 100 μm, e.g., from about 100 μm to about 1,000 μm, e.g., about 200 μm, 300 μm, 400 μm, 500 μm, 600 μm, 700 μm, 800 μm, 900 μm, or 1,000 μm, e.g., from about 1 mm to about 10 mm, e.g., about 2 mm, 3 mm, 4 mm, 5 mm, 6 mm, 7 mm, 8 mm, 9 mm, or 10 mm).

The voids may be arranged, e.g., in a grid pattern. The arrangement of the voids may be determined, e.g., empirically, based on the size of the particle (e.g., a cell) or macromolecular constituent thereof being sorted or separated. The voids may be spaced apart at a predetermined distance from about 1 nm to about 10 mm (e.g., from about 10 nm to about 100 μm, e.g., from about 10 nm to about 1 μm, from about 5 μm to about 10 μm, or from about 10 μm to about 50 μm). For example, the voids may be spaced at a predetermined distance of from about 1 nm to about 10 nm, e.g., about 1 nm, 2 nm, 3 nm, 4 nm, 5 nm, 6 nm, 7 nm, 8 nm, 9 nm, or 10 nm, e.g., from about 10 nm to about 100 nm, e.g., about 20 nm, 30 nm, 40 nm, 50 nm, 60 nm, 70 nm, 80 nm, 90 nm, or 100 nm, e.g., from about 100 nm to about 1,000 nm, e.g., about 1 μm, 2 μm, 3 μm, 4 μm, 5 μm, 6 μm, 7 μm, 8 μm, 9 μm, or 10 μm, e.g., from about 10 μm to about 100 μm, e.g., 20 μm, 30 μm, 40 μm, 50 μm, 60 μm, 70 μm, 80 μm, 90 μm, or 100 μm, e.g., from about 100 μm to about 1,000 μm, e.g., about 200 μm, 300 μm, 400 μm, 500 μm, 600 μm, 700 μm, 800 μm, 900 μm, or 1,000 μm, e.g., from about 1 mm to about 10 mm, e.g., about 2 mm, 3 mm, 4 mm, 5 mm, 6 mm, 7 mm, 8 mm, 9 mm, or 10 mm. In one embodiment, the voids are spaced, e.g., from about 5 μm to about 10 μm, to sort or separate smaller cells, such as blood cells (e.g., erythrocytes). In one embodiment, the voids are spaced, e.g., from about 10 μm to about 50 μm, e.g., to sort or separate larger cells. If a nucleic acid (e.g., DNA or RNA) is being sorted or separated, the spacing may be limited, e.g., by the size of the magnetic particles (e.g., «1 μm, e.g., about 1 nm).

The flow module may contain at least one void. The flow module may contain a plurality of voids. For example, the magnetic module may contain at least 1, 2, 3, 4, 5, 6, 7, 8, 9, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, or more voids.

The voids in the flow module are bounded by a non-magnetic wall that separates the fluid that flows through the flow module and the magnetic features. The wall may have a thickness of from about 10 μm to about 10 mm (e.g., from about 10 μm to about 1 mm, from about 10 μm to about 100 μm, from about 50 μm to about 100 μm, from about 100 μm to about 10 mm, from about 1 mm to about 10 mm, from about 500 μm to about 1 mm, from about 1 mm to about 5 mm, from about 1 mm to about 2 mm, e.g., about 1.5 mm). In some embodiments, the wall may have thickness of from about 10 μm to about 100 μm, e.g., about 10 μm, 20 μm, 30 μm, 40 μm, 50 μm, 60 μm, 70 μm, 80 μm, 90 μm, or 100 μm, e.g., from about 100 μm to about 1000 μm, e.g., about 200 μm, 300 μm, 400 μm, 500 μm, 600 μm, 700 μm, 800 μm, 900 μm, or 1000 μm, e.g., from about 1 mm to about 10 mm, e.g., 2 mm, 3 mm, 4 mm, 5 mm, 6 mm, 7 mm, 8 mm, 9 mm, or 10 mm.

The flow module can be made of any suitable material, such as plastic, glass, or a combination thereof. Suitable materials include, for example, polymers, such as acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Other materials include ceramics, glasses, and non-magnetizable metals (e.g., silicon).

Collection Region

The invention provides systems that may include a collection region. A collection region includes one or more partitions to receive particles from an outlet of the flow module. A collection region or the one or more partitions within a collection region can be of any suitable geometry and may be or include, for example, a well, channel, reservoir, or portion thereof, or the like. The collection region can be open-ended (e.g., connected to subsequent partitions, e.g., channels or reservoirs) or enclosed. The collection region may include one or more (e.g., 2, 3, 4, 5, 6, 7, 8, 9, 10, 20, 30, 40, 50, 60, 70, 80, 90, 100, 200, 300, 400, 500, 600, 700, 800, 900, 1000, or more) partitions (e.g., channels or reservoirs) configured to receive the magnetic particles or other particles (e.g., waste or debris) after separation. The one or more partitions in the collection region can have any length, width, and height suitable for receiving one or more particles. For example, the length, width, and height may be independently, from about 1 µm to about 10 mm (e.g., 1 µm, 2 µm, 3 µm, 4 µm, 5 µm, 6 µm, 7 µm, 8 µm, 9 µm, or 10 µm, e.g., from about 10 µm to about 100 µm, e.g., 20 µm, 30 µm, 40 µm, 50 µm, 60 µm, 70 µm, 80 µm, 90 µm, or 100 µm, e.g., from about 100 µm to about 1,000 µm, e.g., 200 µm, 300 µm, 400 µm, 500 µm, 600 µm, 700 µm, 800 µm, 900 µm, or 1,000 µm, e.g., from about 1 mm to about 10 mm, e.g., 2 mm, 3 mm, 4 mm, 5 mm, 6 mm, 7 mm, 8 mm, 9 mm, or 10 mm). In some embodiments, the collection region has no cross-sectional dimension of less than 1 mm. For example, each cross-sectional dimension of the collection region has a length of at least 1 mm (e.g., 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, 100 mm, or more). The one or more partitions may have one or more dividers between them to physically separate the sorted particles. A divider may be any feature that can obstruct or prevent the droplets or particles from moving into a different partition, thereby unsorting the sorted particles. A divider may be an insert in or between partitions or may be, e.g., a hollow cylindrical or partially cylindrical insert configured to fit within a cylindrical well. For example, a collection region may include multiple adjacent partitions, with each partition separated from its neighboring partition by a divider. This provides separation between the partitions so that the particles within each partition cannot mix with the particles in the neighboring partition, and the sorted populations of particles are maintained as separate populations.

Sample

The samples that may be used with the systems described herein may be any liquid, e.g., an aqueous or non-aqueous liquid, that contains suspended magnetic particles. The magnetic particles may be attached to other particles, e.g., biological particles, e.g., a cell, a nucleus, or a macromolecular constituent thereof, e.g., an organelle or nucleic acid, or otherwise soluble substances, e.g., proteins, nucleic acids, etc. The sample may be provided to the flow module via a sample holder, e.g., which is in fluid communication with an inlet of the flow module. The sample holder may be any suitable geometry, such as a well, channel, reservoir, tube, or portion thereof, and the like. The sample holder may be, for example, a microcentrifuge tube or a PCR tube.

The systems described herein may be advantageous for small volumes of sample (e.g., less than 100 µL, 90 µL, 80 µL, 70 µL, 60 µL, 50 µL, 40 µL, 30 µL, 20 µL, 10 µL, 9 µL, 8 µL, 7 µL, 6 µL, 5 µL, 4 µL, 3 µL, 2 µL or 1 µL), or volumes of samples that contain a low number of magnetic particles (e.g., that are attached to a desired biological particle, e.g., a cell, a nucleus, or macromolecular constituent thereof). For example, the sample holder may contain a sample with fewer than 1,000, e.g., less than 900, 800, 700, 600, 500, 400, 300, 200, or 100, magnetic particles.

The samples may be used for preparation before incorporation into droplets. Alternatively, the samples may be derived from droplets, e.g., following breaking or destabilization of droplets. Droplets generally refer to one liquid suspended in a second immiscible liquid and may be formed in which one or more magnetic particles are encapsulated within the droplet.

In general, droplets may be formed by shaking or stirring a liquid to form individual droplets, creating a suspension or an emulsion containing individual droplets, or forming the droplets through pipetting techniques, e.g., with needles, or the like. The droplets may be formed made using a micro-, or nanofluidic droplet maker. Examples of such droplet makers include, e.g., a T-junction droplet maker, a Y-junction droplet maker, a channel-within-a-channel junction droplet maker, a cross (or "X") junction droplet maker, a flow-focusing junction droplet maker, a micro-capillary droplet maker (e.g., co-flow or flow-focus), and a three-dimensional droplet maker. The droplets may be produced using a flow-focusing device, or with emulsification systems, such as homogenization, membrane emulsification, shear cell emulsification, and fluidic emulsification. Droplets may also be formed as described in WO 2019/040637.

Discrete liquid droplets may be encapsulated by a carrier fluid that wets the microchannel. These droplets, sometimes known as plugs, form the dispersed phase in which the reactions occur. Systems that use plugs differ from segmented-flow injection analysis in that reagents in plugs do not come into contact with the microchannel. In T junctions, the disperse phase and the continuous phase are injected from two branches of the "T". Droplets of the disperse phase are produced as a result of the shear force and interfacial tension at the fluid-fluid interface. The phase that has lower interfacial tension with the channel wall is the continuous phase. To generate droplets in a flow-focusing configuration, the continuous phase is injected through two outside channels and the disperse phase is injected through a central channel into a narrow orifice. Other geometric designs to create droplets would be known to one of skill in the art. Methods of producing droplets are disclosed in Song et al. Angew. Chem. 45: 7336-7356, 2006, Mazutis et al. Nat. Protoc. 8(5):870-891, 2013, U.S. Pat. No. 9,839,911; U.S. Pub. Nos. 2005/0172476, 2006/0163385, and 2007/0003442, PCT Pub. Nos. WO 2009/005680 and WO 2018/009766. In some embodiments, electric fields or acoustic waves may be used to produce droplets, e.g., as described in PCT Pub. No. WO 2018/009766.

Surface Properties

A surface of the system may include a material, coating, or surface texture that determines the physical properties of the system. In particular, the flow of liquids through a system of the invention may be controlled by the system surface properties (e.g., wettability of a liquid-contacting surface). In some cases, a system portion (e.g., a flow module, void, or wall) may have a surface having a wettability suitable for facilitating liquid flow (e.g., in a channel) or assisting droplet formation of a first liquid in a second liquid (e.g., in a channel), e.g., if droplet formation is performed.

Wetting, which is the ability of a liquid to maintain contact with a solid surface, may be measured as a function of a water contact angle. A water contact angle of a material can be measured by any suitable method known in the art, such as the static sessile drop method, pendant drop method, dynamic sessile drop method, dynamic Wilhelmy method, single-fiber Wilhelmy method, single-fiber meniscus method, and Washburn's equation capillary rise method. The wettability of each surface may be suited to separating magnetic particles, e.g., coupled to cells, nuclei, or particulate components thereof.

For example, portions of the system carrying aqueous phases (e.g., a flow module, void, or wall) may have a surface material or coating that is hydrophilic or more hydrophilic than another portion of the system, e.g., include a material or coating having a water contact angle of less than or equal to about 90°, and/or another portion of the system may have a surface material or coating that is hydrophobic or more hydrophobic than the channel, e.g., include a material or coating having a water contact angle of greater than 70° (e.g., greater than 90°, greater than 95°, greater than 100° (e.g., 95°-120° or 100°-10°)). In certain embodiments, a portion of the system may include a material or surface coating that reduces or prevents wetting by aqueous phases. The system can be designed to have a single type of material or coating throughout. Alternatively, the system may have separate regions having different materials or coatings.

The system surface properties may be those of a native surface (i.e., the surface properties of the bulk material used for the system fabrication) or of a surface treatment. Non-limiting examples of surface treatments include, e.g., surface coatings and surface textures. In one approach, the system surface properties are attributable to one or more surface coatings present in a system portion. Hydrophobic coatings may include fluoropolymers (e.g., AQUAPEL® glass treatment), silanes, siloxanes, silicones, or other coatings known in the art. Other coatings include those vapor deposited from a precursor such as henicosyl-1,1,2,2-tetrahydrododecyldimethyltris(dimethylaminosilane); henicosyl-1,1,2,2-tetrahydrododecyltrichlorosilane (C12); heptadecafluoro-1,1,2,2-tetrahydrodecyltrichlorosilane (C10); nonafluoro-1,1,2,2-tetrahydrohexyltris(dimethylamino)silane; 3,3,3,4,4,5,5,6,6-nonafluorohexyltrichlorosilane; tridecafluoro-1,1,2,2-tetrahydrooctyltrichlorosilane (C8); bis(tridecafluoro-1,1,2,2-tetrahydrooctyl)dimethylsiloxymethylchlorosilane; nonafluorohexyltriethoxysilane (C6); dodecyltrichlorosilane (DTS); dimethyldichlorosilane (DDMS); or 10-undecenyltrichlorosilane (V11); pentafluorophenylpropyltrichlorosilane (C5). Hydrophilic coatings include polymers such as polysaccharides, polyethylene glycol, polyamines, and polycarboxylic acids. Hydrophilic surfaces may also be created by oxygen plasma treatment of certain materials.

A coated surface may be formed by depositing a metal oxide onto a surface of the system. Example metal oxides useful for coating surfaces include, but are not limited to, $Al_2O_3$, $TiO_2$, $SiO_2$, or a combination thereof. Other metal oxides useful for surface modifications are known in the art. The metal oxide can be deposited onto a surface by standard deposition techniques, including, but not limited to, atomic layer deposition (ALD), physical vapor deposition (PVD), e.g., sputtering, chemical vapor deposition (CVD), or laser deposition. Other deposition techniques for coating surfaces, e.g., liquid-based deposition, are known in the art. For example, an atomic layer of $Al_2O_3$ can be deposited on a surface by contacting it with trimethylaluminum (TMA) and water.

In another approach, the system surface properties may be attributable to surface texture. For example, a surface may have a nanotexture, e.g., have a surface with nanometer surface features, such as cones or columns, that alters the wettability of the surface. Nanotextured surface may be hydrophilic, hydrophobic, or superhydrophobic, e.g., have a water contact angle greater than 150°. Exemplary superhydrophobic materials include Manganese Oxide Polystyrene ($MnO_2$/PS) nano-composite, Zinc Oxide Polystyrene (ZnO/PS) nano-composite, Precipitated Calcium Carbonate, Carbon nano-tube structures, and a silica nano-coating. Superhydrophobic coatings may also include a low surface energy material (e.g., an inherently hydrophobic material) and a surface roughness (e.g., using laser ablation techniques, plasma etching techniques, or lithographic techniques in which a material is etched through apertures in a patterned mask). Examples of low surface energy materials include fluorocarbon materials, e.g., polytetrafluoroethylene (PTFE), fluorinated ethylene propylene (FEP), ethylene tetrafluoroethylene (ETFE), ethylene chloro-trifluoroethylene (ECTFE), perfluoro-alkoxyalkane (PFA), poly(chloro-trifluoro-ethylene) (CTFE), perfluoro-alkoxyalkane (PFA), and poly(vinylidene fluoride) (PVDF). Other superhydrophobic surfaces are known in the art.

In some cases, the water contact angle of a hydrophilic or more hydrophilic material or coating is less than or equal to about 90°, e.g., less than 80°, 70°, 60°, 50°, 40°, 30°, 20°, or 10°, e.g., 90°, 85°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, or 0°. In some cases, the water contact angle of a hydrophobic or more hydrophobic material or coating is at least 70°, e.g., at least 80°, at least 85°, at least 90°, at least 95°, or at least 100° (e.g., about 100°, 101°, 102°, 103°, 104°, 105°, 106°, 107°, 108°, 109°, 110°, 115°, 120°, 125°, 130°, 135°, 140°, 145°, or about) 150°.

The difference in water contact angles between that of a hydrophilic or more hydrophilic material or coating and a hydrophobic or more hydrophobic material or coating may be 5° to 100°, e.g., 5° to 80°, 5° to 60°, 5° to 50°, 5° to 40°, 5° to 30°, 5° to 20°, 10° to 75°, 15° to 70°, 20° to 65°, 25° to 60°, 30 to 50°, 35° to 45°, e.g., 5°, 6°, 7°, 8°, 9°, 10°, 15°, 20°, 25°, 30°, 35°, 40°, 45°, 50°, 55°, 60, 65°, 70°, 75°, 80°, 85°, 90°, or 100°.

The above discussion centers on the water contact angle. It will be understood that liquids employed in the systems and methods of the invention may not be water, or even aqueous. Accordingly, the actual contact angle of a liquid on a surface of the system may differ from the water contact angle. Furthermore, the determination of a water contact angle of a material or coating can be made on that material or coating when not incorporated into a system of the invention.

Particles

The invention includes systems and kits having particles, e.g., for use in analysis. The devices and systems are used for magnetic separation of samples containing magnetic particles. The samples may further include non-magnetic particles, e.g., attached to the magnetic particles. For example, particles configured with analyte moieties (e.g., barcodes, nucleic acids, binding molecules (e.g., proteins, peptides, aptamers, antibodies, or antibody fragments), enzymes, substrates, etc.) can be included in a droplet containing an analyte to modify the analyte and/or detect the presence or concentration of the analyte. In some embodiments, particles are synthetic particles (e.g., beads, e.g., gel beads).

Magnetic particles include at least one component that is responsive to a magnetic force. A magnetic particle may be entirely magnetic or may contain components that are non-magnetic. A magnetic particle may be a magnetic bead, e.g., a substantially spherical magnetic bead. The magnetic particle may be entirely magnetic or may contain one or more magnetic cores surrounded by one or more additional materials, such as, for example, one or more functional groups and/or modifications for binding one or more target molecules.

In some examples, a magnetic particle may contain a magnetic component and a surface modified with one or more silanol groups. Magnetic particles of this type may be used for binding target nucleic acid molecules. Silanol-modified magnetic beads are commercially available (Accu Bead silica-coated magnetic beads available from Bioneer, silane-modified Dynabeads available from Life Technologies, MagSi beads available from AMSBIO, among others). A magnetic particle may be a magnetic bead or particle and the surface may be functionalized with a plurality of carboxyl groups. Such magnetic particles can make use of solid phase reverse immobilization (SPRI) technology. Carboxylated magnetic beads are available from commercial sources, for example, Agencourt AMPure XP SPRI beads available from Beckman-Coulter.

In some examples, a magnetic particle may be coated with a surface modified with a moiety to trap certain desired or undesired particles or macromolecular constituents thereof, such as a nucleic acid (e.g., RNA, DNA, or a combination thereof) or other biological particles (e.g., live cell, dead cell, or cellular debris). A magnetic particle may be coated with an antibody or antigen-binding fragment thereof to capture a cellular antigen (e.g., surface marker). A magnetic particle may be coated with positively charged moieties to capture nucleic acids, such as DNA and/or RNA.

Magnetic materials may be classified according to their magnetic properties. Without wishing to be bound by theory, materials can generally be classified as diamagnetic, paramagnetic, or ferromagnetic. Diamagnetism is a property of all materials and can be a weak magnetic force. Diamagnetic materials can create an induced magnetic field in a direction opposite to an externally applied magnetic field. Paramagnetic materials can be attracted by an externally applied magnetic field and form induced magnetic fields in the direction of the applied magnetic field. Ferromagnetic materials are those that can be become permanently magnetized in the presence of a magnetic field. Examples of magnetic materials that may be included in a magnetic particle include iron, nickel, cobalt, composites thereof and alloys thereof. In some instances, a magnetic material may include one or more iron-oxides, such as magnetite or maghemite.

A particle, e.g., a magnetic particle or a bead, may be porous, non-porous, hollow (e.g., a microcapsule), solid, semi-solid, semi-fluidic, fluidic, and/or a combination thereof. In some instances, a particle, e.g., a bead, may be dissolvable, disruptable, and/or degradable. In some cases, a particle, e.g., a bead, may not be degradable. In some cases, the particle, e.g., a bead, may be a gel bead. A gel bead may be a hydrogel bead. A gel bead may be formed from molecular precursors, such as a polymeric or monomeric species. A semi-solid particle, e.g., a bead, may be a liposomal bead. Solid particles, e.g., beads, may comprise metals including iron oxide, gold, and silver. In some cases, the particle, e.g., the bead, may be a silica bead. In some cases, the particle, e.g., a bead, can be rigid. In other cases, the particle, e.g., a bead, may be flexible and/or compressible.

A particle, e.g., a magnetic particle or a bead, may comprise natural and/or synthetic materials. For example, a particle, e.g., a bead, can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

In some instances, the particle, e.g., the magnetic particle or bead, may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the particle, e.g., the bead, may comprise prepolymers, which are oligomers capable of further polymerization. For example, polyurethane beads may be prepared using prepolymers. In some cases, the particle, e.g., the bead, may contain individual polymers that may be further polymerized together. In some cases, particles, e.g., beads, may be generated via polymerization of different precursors, such that they comprise mixed polymers, co-polymers, and/or block co-polymers. In some cases, the particle, e.g., the bead, may comprise covalent or ionic bonds between polymeric precursors (e.g., monomers, oligomers, linear polymers), oligonucleotides, primers, and other entities. In some cases, the covalent bonds can be carbon-carbon bonds or thioether bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

Particles, e.g., magnetic particles or beads, may be of uniform size or heterogeneous size. In some cases, the diameter of a particle, e.g., a bead, may be at least about 1 micrometer (μm), 5 μm, 10 μm, 20 μm, 30 μm, 40 μm, 50 μm, 60 μm, 70 μm, 80 μm, 90 μm, 100 μm, 250 μm, 500 μm, 1 mm, or greater. In some cases, a particle, e.g., a bead, may have a diameter of less than about 1 μm, 5 μm, 10 μm, 20 μm, 30 μm, 40 μm, 50 μm, 60 μm, 70 μm, 80 μm, 90 μm, 100 μm, 250 μm, 500 μm, 1 mm, or less. In some cases, a particle, e.g., a bead, may have a diameter in the range of about 40-75 μm, 30-75 μm, 20-75 μm, 40-85 μm, 40-95 μm, 20-100 μm, 10-100 μm, 1-100 μm, 20-250 μm, or 20-500 μm. The size of a particle, e.g., a bead, e.g., a gel bead, used to produce droplets is typically on the order of a cross section of the first channel (width or depth). In some cases, the gel beads are larger than the width and/or depth of the first channel and/or shelf, e.g., at least 1.5×, 2×, 3×, or 4× larger than the width and/or depth of the first channel and/or shelf.

In certain embodiments, particles, e.g., magnetic particles or beads, can be provided as a population or plurality of particles, e.g., beads, having a relatively monodisperse size distribution. Where it may be desirable to provide relatively consistent amounts of reagents within droplets, maintaining relatively consistent particle, e.g., bead, characteristics, such as size, can contribute to the overall consistency. In particular, the particles, e.g., beads, described herein may have size distributions that have a coefficient of variation in their cross-sectional dimensions of less than 50%, less than 40%, less than 30%, less than 20%, and in some cases less than 15%, less than 10%, less than 5%, or less.

Particles may be of any suitable shape. Examples of particles, e.g., magnetic particles or beads, shapes include, but are not limited to, spherical, non-spherical, oval, oblong, amorphous, circular, cylindrical, and variations thereof.

A particle, e.g., magnetic particle or bead, may comprise releasably, cleavably, or reversibly attached analyte moieties (e.g., barcodes). A particle, e.g., bead, may comprise activatable analyte moieties (e.g., barcodes). A particle, e.g., bead may be a degradable, disruptable, or dissolvable particle, e.g., dissolvable bead.

As discussed above, analyte moieties (e.g., barcodes) can be releasably, cleavably or reversibly attached to the particles, e.g., beads, such that analyte moieties (e.g., barcodes) can be released or be releasable through cleavage of a linkage between the barcode molecule and the particle, e.g., bead, or released through degradation of the particle (e.g., bead) itself, allowing the barcodes to be accessed or be accessible by other reagents, or both. Releasable analyte moieties (e.g., barcodes) may sometimes be referred to as activatable analyte moieties (e.g., activatable barcodes), in that they are available for reaction once released. Thus, for example, an activatable analyte moiety (e.g., activatable barcode) may be activated by releasing the analyte moiety (e.g., barcode) from a particle, e.g., bead (or other suitable type of droplet described herein). Other activatable configurations are also envisioned in the context of the described methods and systems.

In addition to, or as an alternative to the cleavable linkages between the particles, e.g., magnetic particles or beads, and the associated moieties, such as barcode containing nucleic acids (e.g., oligonucleotides), the particles, e.g., beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a particle, e.g., bead, may be dissolvable, such that material components of the particle, e.g., bead, are degraded or solubilized when exposed to a particular chemical species or an environmental change, such as a change temperature or a change in pH. In some cases, a gel bead can be degraded or dissolved at elevated temperature and/or in basic conditions. In some cases, a particle, e.g., bead, may be thermally degradable such that when the particle, e.g., bead, is exposed to an appropriate change in temperature (e.g., heat), the particle, e.g., bead, degrades. Degradation or dissolution of a particle (e.g., bead) bound to a species (e.g., a nucleic acid, e.g., an oligonucleotide, e.g., barcoded oligonucleotide) may result in release of the species from the particle, e.g., bead. As will be appreciated from the above disclosure, the degradation of a particle, e.g., bead, may refer to the disassociation of a bound or entrained species from a particle, e.g., bead, both with and without structurally degrading the physical particle, e.g., bead, itself. For example, entrained species may be released from particles, e.g., beads, through osmotic pressure differences due to, for example, changing chemical environments. By way of example, alteration of particle, e.g., bead, pore sizes due to osmotic pressure differences can generally occur without structural degradation of the particle, e.g., bead, itself. In some cases, an increase in pore size due to osmotic swelling of a particle, e.g., bead or microcapsule (e.g., liposome), can permit the release of entrained species within the particle. In other cases, osmotic shrinking of a particle may cause the particle, e.g., bead, to better retain an entrained species due to pore size contraction.

Any suitable number of analyte moieties (e.g., molecular tag molecules (e.g., primer, barcoded oligonucleotide, etc.)) can be associated with a particle, e.g., bead, such that, upon release from the particle, the analyte moieties (e.g., molecular tag molecules (e.g., primer, e.g., barcoded oligonucleotide, etc.)) are present in the droplet at a pre-defined concentration. Such pre-defined concentration may be selected to facilitate certain reactions for generating a sequencing library, e.g., amplification, within the droplet. In some cases, the pre-defined concentration of a primer can be limited by the process of producing oligonucleotide-bearing particles, e.g., beads.

Additional reagents may be included as part of the particles (e.g., analyte moieties), for example, to activate, mediate, or otherwise participate in a reaction, e.g., between the analyte and analyte moiety.

Biological Samples

Samples may include biological particles (e.g., cells or particulate components thereof, e.g., organelles, such as a nucleus or a mitochondrion) and/or macromolecular constituents thereof (e.g., components of cells (e.g., intracellular or extracellular proteins, nucleic acids, glycans, or lipids) or products of cells (e.g., secretion products)). An analyte from a biological particle, e.g., component or product thereof, may be considered to be a bioanalyte. In some embodiments, a biological particle, e.g., cell, or product thereof is included in a droplet, e.g., with one or more particles (e.g., beads) having an analyte moiety. A biological particle, e.g., cell, a nucleus, and/or components or products thereof can, in some embodiments, be encased inside a gel, such as via polymerization of a droplet containing the biological particle and precursors capable of being polymerized or gelled.

In the case of encapsulated biological particles (e.g., cells, nuclei, or particulate components thereof), a biological particle may be included in a droplet that contains lysis reagents in order to release the contents (e.g., contents containing one or more analytes (e.g., bioanalytes)) of the biological particles within the droplet. In such cases, the lysis agents can be contacted with the biological particle suspension concurrently with, or immediately prior to the introduction of the biological particles into a droplet or particle. Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), as well as other commercially available lysis enzymes. Other lysis agents may additionally or alternatively be contained in a droplet with the biological particles (e.g., cells, nuclei, or particulate components thereof) to cause the release of the biological particles' contents into the droplets or particles. For example, in some cases, surfactant based lysis solutions may be used to lyse cells, although these may be less desirable for emulsion based systems where the surfactants can interfere with stable emulsions. In some cases, lysis solutions may include non-ionic surfactants such as, for example, TRITON X-100 and TWEEN 20. In some cases, lysis solutions may include ionic surfactants such as, for example, sarcosyl and sodium dodecyl sulfate (SDS). In some embodiments, lysis solutions are hypotonic, thereby lysing cells by osmotic shock. Electroporation, thermal, acoustic or mechanical cellular disruption may also be used in certain cases, e.g., non-emulsion-based droplet formation such as encapsulation of biological particles that may be in addition to or in place of droplet formation, where any pore size of the encapsulate is sufficiently small to retain nucleic acid fragments of a desired size, following cellular disruption.

In addition to the lysis agents, other reagents can also be included in droplets with the biological particles, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated biological particles (e.g., cells, nuclei, or particulate components thereof), the biological particles may be exposed to an appropriate stimulus to release the biological particles or their contents from a microcapsule within a droplet. For example, in some cases, a chemical stimulus may be included in a droplet along with an encapsulated biological particle to allow for degradation of the encapsulating matrix and release of the cell or its contents into the larger droplet. In some cases, this stimulus may be the same as the stimulus described elsewhere herein for release of analyte moieties (e.g., oligonucleotides) from their respective particle (e.g., bead). In alternative aspects, this may be a different and non-overlapping stimulus, in order to allow an encapsulated biological particle to be released into a droplet at a different time from the release of analyte moieties (e.g., oligonucleotides) into the same droplet.

Additional reagents may also be included in droplets with the biological particles, such as endonucleases to fragment a biological particle's DNA, DNA polymerase enzymes and dNTPs used to amplify the biological particle's nucleic acid fragments and to attach the barcode molecular tags to the amplified fragments. Other reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyinosine, Super T (5-hydroxybutynl-2'-deoxyuridine), Super G (8-aza-7-deaz-aguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250 nucleotides or longer.

In some cases, the length of a switch oligo may be at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells or nuclei are released into their respective droplets, the macromolecular components (e.g., macromolecular constituents of biological particles, such as RNA, DNA, or proteins) contained therein may be further processed.

As described above, the macromolecular components (e.g., bioanalytes) of individual biological particles (e.g., cells, nuclei, or particulate components thereof) can be provided with unique identifiers (e.g., barcodes) such that upon characterization of those macromolecular components, at which point components from a heterogeneous population of cells or nuclei may have been mixed and are interspersed or solubilized in a common liquid, any given component (e.g., bioanalyte) may be traced to the biological particle (e.g., cell or nucleus) from which it was obtained. The ability to attribute characteristics to individual biological particles or groups of biological particles is provided by the assignment of unique identifiers specifically to an individual biological particle or groups of biological particles. Unique identifiers, for example, in the form of nucleic acid barcodes, can be assigned or associated with individual biological particles (e.g., cells, nuclei, or particulate components thereof) or populations of biological particles (e.g., cells or nuclei), in order to tag or label the biological particle's macromolecular components (and as a result, its characteristics) with the unique identifiers. These unique identifiers can then be used to attribute the biological particle's components and characteristics to an individual biological particle or group of biological particles. This can be performed by forming droplets including the individual biological particle or groups of biological particles with the unique identifiers (via particles, e.g., beads), as described in the systems and methods herein.

In some aspects, the unique identifiers are provided in the form of oligonucleotides that comprise nucleic acid barcode sequences that may be attached to or otherwise associated with the nucleic acid contents of individual biological particle, or to other components of the biological particle, and particularly to fragments of those nucleic acids. The oligonucleotides are partitioned such that as between oligonucleotides in a given droplet, the nucleic acid barcode sequences contained therein are the same, but as between different droplets, the oligonucleotides can, and do have differing barcode sequences, or at least represent a large number of different barcode sequences across all of the droplets in a given analysis. In some aspects, only one nucleic acid barcode sequence can be associated with a given droplet, although in some cases, two or more different barcode sequences may be present.

The nucleic acid barcode sequences can include from 6 to about 20 or more nucleotides within the sequence of the oligonucleotides. In some cases, the length of a barcode sequence may be 6, 7, 8, 9, 10, 11, 12, 13, 14, 15, 16, 17, 18, 19, 20 nucleotides or longer. In some cases, the length of a barcode sequence may be at least 6, 7, 8, 9, 10, 11, 12, 13, 14, 15, 16, 17, 18, 19, 20 nucleotides or longer. In some cases, the length of a barcode sequence may be at most 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be 4, 5, 6, 7, 8, 9, 10, 11, 12, 13, 14, 15, 16 nucleotides or longer. In some cases, the barcode subsequence may be at least 4, 5, 6, 7, 8, 9, 10, 11, 12, 13, 14, 15, 16 nucleotides or longer. In some cases, the barcode subsequence may be at most 4, 5, 6, 7, 8, 9, 10, 11, 12, 13, 14, 15, 16 nucleotides or shorter.

Analyte moieties (e.g., oligonucleotides) in droplets can also include other functional sequences useful in processing of nucleic acids from biological particles contained in the droplet. These sequences include, for example, targeted or random/universal amplification primer sequences for amplifying the genomic DNA from the individual biological particles within the droplets while attaching the associated barcode sequences, sequencing primers or primer recognition sites, hybridization or probing sequences, e.g., for identification of presence of the sequences or for pulling down barcoded nucleic acids, or any of a number of other potential functional sequences.

Other mechanisms of forming droplets containing oligonucleotides may also be employed, including, e.g., coalescence of two or more droplets, where one droplet contains oligonucleotides, or microdispensing of oligonucleotides into droplets, e.g., droplets within microfluidic systems.

In an example, particles (e.g., magnetic particles or beads) are provided that each include large numbers of the above described barcoded oligonucleotides releasably attached to the beads, where all of the oligonucleotides attached to a particular bead will include the same nucleic acid barcode sequence, but where a large number of diverse barcode sequences are represented across the population of beads used. In some embodiments, hydrogel beads, e.g., beads having polyacrylamide polymer matrices, are used as a solid support and delivery vehicle for the oligonucleotides into the droplets, as they are capable of carrying large numbers of oligonucleotide molecules and may be configured to release those oligonucleotides upon exposure to a particular stimulus, as described elsewhere herein. In some cases, the population of beads will provide a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of oligonucleotide molecules attached. In particular, the number of molecules of oligonucleotides including the barcode sequence on an individual bead can be at least about 1,000 oligonucleotide molecules, at least about 5,000 oligonucleotide molecules, at least about 10,000 oligonucleotide molecules, at least about 50,000 oligonucleotide molecules, at least about 100,000 oligonucleotide molecules, at least about 500,000 oligonucleotides, at least about 1,000,000 oligonucleotide molecules, at least about 5,000,000 oligonucleotide molecules, at least about 10,000,000 oligonucleotide molecules, at least about 50,000,000 oligonucleotide molecules, at least about 100,000,000 oligonucleotide molecules, and in some cases at least about 1 billion oligonucleotide molecules, or more.

Moreover, when the population of magnetic particles or beads are included in droplets, the resulting population of droplets can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each droplet of the population can include at least about 1,000 oligonucleotide molecules, at least about 5,000 oligonucleotide molecules, at least about 10,000 oligonucleotide molecules, at least about 50,000 oligonucleotide molecules, at least about 100,000 oligonucleotide molecules, at least about 500,000 oligonucleotides, at least about 1,000,000 oligonucleotide molecules, at least about 5,000,000 oligonucleotide molecules, at least about 10,000,000 oligonucleotide molecules, at least about 50,000,000 oligonucleotide molecules, at least about 100,000,000 oligonucleotide molecules, and in some cases at least about 1 billion oligonucleotide molecules.

In some cases, it may be desirable to incorporate multiple different barcodes within a given droplet, either attached to a single particle or multiple particles, e.g., beads, within the droplet. For example, in some cases, mixed, but known barcode sequences set may provide greater assurance of identification in the subsequent processing, for example, by providing a stronger address or attribution of the barcodes to a given droplet, as a duplicate or independent confirmation of the output from a given droplet.

Oligonucleotides may be releasable from the particles (e.g., beads) upon the application of a particular stimulus. In some cases, the stimulus may be a photo-stimulus, e.g., through cleavage of a photo-labile linkage that releases the oligonucleotides. In other cases, a thermal stimulus may be used, where increase in temperature of the particle, e.g., bead, environment will result in cleavage of a linkage or other release of the oligonucleotides form the particles, e.g., beads. In still other cases, a chemical stimulus is used that cleaves a linkage of the oligonucleotides to the beads, or otherwise results in release of the oligonucleotides from the particles, e.g., magnetic particles or beads. In one case, such compositions include the polyacrylamide matrices described above for encapsulation of biological particles and may be degraded for release of the attached oligonucleotides through exposure to a reducing agent, such as dithiothreitol (DTT).

Kits

Systems of the invention may be combined with various external components in the form of kits. For example, a kit may include a system of the invention and, e.g., one or more sample holders, magnetic sources, e.g., magnets and/or magnetic fluids, samples, magnetic particles, and the like. The kit may include a plurality of magnets and/or magnetic fluids. The kits may further include, e.g., electrodes, pumps, reservoirs, controllers, reagents, e.g., analyte moieties, liquids, and/or particles (e.g., beads).

Methods

The methods of magnetic separation described herein are used for separating or sorting particles in a liquid by providing a system that includes a magnetic module with a plurality of magnetic features and a flow module with a plurality of voids around which fluid can flow. The flow module is configured to mate with the magnetic module, and the two modules can be removably attached. The method may include providing a sample that contains a liquid with suspended magnetic particles. The sample is allowed to enter the flow module, e.g., via an inlet, and the magnetic particles within the sample are attracted to one or more of the magnetic features.

The method may further include washing the magnetic particles, e.g., to remove non-magnetic particles or debris. Washing may include flowing a second liquid into the flow module. The method may include resuspending the magnetic particles in a second liquid, e.g., to produce a sample that is enriched in the magnetic particles. Washing and/or resuspending the particles may be performed one or more times, e.g., to serially enrich or purify the magnetic particles. The method may further include eluting the magnetic particles, e.g., by removing the magnetic module from the flow module. The magnetic particles may flow through an outlet, such that a collection region or a partition therein in fluid communication with that particular outlet collects a sample enriched in the magnetic particles. Alternatively, if the magnetic particles do not flow out of the channel by fluid flow, the magnet or magnetic module may be removed to eliminate or reduce the magnetic gradient on the magnetic particles. For example, the magnetic module is removed so that the magnetic features no longer mate with the voids in the flow module, thereby eliminating or reducing the gradient on the magnetic particles and allowing them to flow out the flow module. The sample containing purified magnetic particles may be subsequently used to produce droplets containing the particles.

The methods described herein may be used to move magnetic particles (e.g., cause spatial separation), separate different species of magnetic particles, or to produce a population enriched in particular magnetic particles from a mixture. For example, the population may be enriched by 10%. The mixture may be enriched (e.g., by 10%, 20%, 30%, 40%, 50%, 60%, 70%, 80%, 100%, 200%, 300%, 400%, 500%, 600%, 700%, 800%, 900%, 1000%, or more) for a subset of the particles. The enrichment of the mixture may be used to remove contaminants or undesired particles in the solution (e.g., solute molecules, insoluble contaminants, debris, soluble components, etc.). Accordingly, the enrichment may be relative to the original mixture.

One or more magnetic particles can be isolated and/or immobilized at a location in the flow module (e.g., adjacent the voids) by applying a magnetic force to the one or more magnetic particles (e.g., magnetic separation). A magnetic force can be applied to one or more magnetic particles by exposing the one or more magnetic particles to an external magnetic field produced by the magnetic features or a magnet coupled to the magnetic features. The magnet may be, for example, a permanent magnetic, electromagnet, or the like. The magnetic responsiveness of a magnetic particle to a magnetic force can be useful in isolating a magnetic particle having bound target from a mixture. Application of a magnetic force to the magnetic particle can result in separation of the magnetic particle from other components in a mixture. Accordingly, any target (e.g., one or more target cells, nuclei, or molecules) that is also bound to the magnetic particle, covalently or non-covalently, can also be separated from non-bound components in a mixture. When an external magnetic field is applied to a magnetic particle, the magnetic particle can be attracted via magnetic force in the direction of the external magnetic field. The magnet and/or the magnetic features can be positioned such that a magnetic particle or a plurality of magnetic particles is attracted to one or more specific locations, e.g., in the flow module, e.g., adjacent the voids. For example, when one or more magnetic particles are provided in a mixture, e.g., via a sample holder to the flow module, the one or more magnetic particles may be positioned at one or more locations (e.g., surfaces) of the flow module. For example, the magnetic particles may be attracted to or immobilized adjacent to the voids. Some magnetic particles may be attracted to one feature and some magnetic particles may be attracted to another feature, e.g., depending on the relative strength of the magnetic gradient from the features and/or the magnet and the position of the magnetic particles within the flow module.

Magnetic immobilization/separation of one or more magnetic particles at multiple positions within a flow module may be used in purification. Magnetic separation at multiple positions within a flow module may occur simultaneously (e.g., one or more magnetic particles simultaneously positioned at a plurality of locations within a channel) or sequentially (e.g., a first round of magnetic separation at a first location, a second round or magnetic separation at a second location, etc.). For example, one or more magnetic particles may be provided to a flow module containing a liquid mixture having contents that contain one or more targets, e.g., following breaking of droplets or for subsequent incorporation into droplets. The one or more magnetic particles can bind the target to provide one or more bound targets. Following binding of targets to the one or more magnetic particles, the one or more magnetic particles can be immobilized at a first location of the flow module via the magnetic features, thereby separating or isolating the one or more magnetic particles (and associated targets) from the mixture. In one embodiment, an external magnetic field may be applied by a magnet coupled to the magnetic features such that a magnetic particle with a bound target within the flow module is attracted or pulled towards the magnetic source. An immobilized magnetic particle can be segregated in a flow module and the movement of the immobilized magnetic particle can be restricted (e.g., to the wall of a void).

Alternatively, magnetic particles are not immobilized but moved towards the magnetic features. A flow module with multiple outlets would allow separation of a portion of the liquid adjacent the voids, which is enriched in magnetic particles, from a non-enriched portion of the liquid.

The methods described herein may include a sample preparation step in which magnetic particles are used to trap desired or undesired particles or macromolecular constituents thereof (e.g., biological particles, e.g., cells, or nucleic acids) before performing magnetic separation using a system as described herein. For example, a magnetic particle may be coated with an antibody or antigen-binding fragment thereof to capture a cellular antigen of a particular cell type (e.g., surface marker). A magnetic particle may be coated with positively charged moieties to capture nucleic acids, e.g., DNA and/or RNA.

Figure 5:
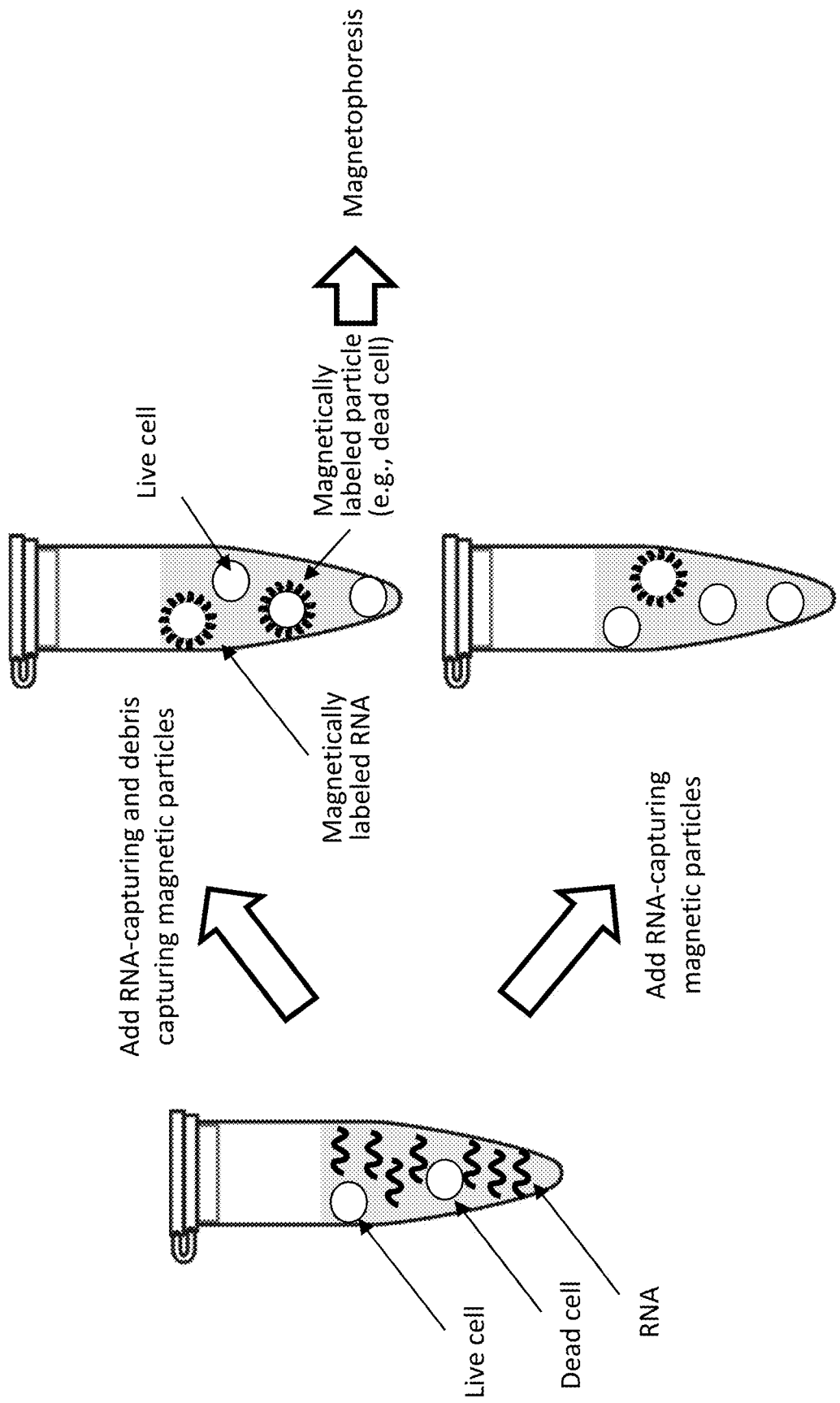
FIG. 5 is a schematic drawing of a sample preparation step in which magnetically labeled particles are used to capture a biological particle or macromolecular constituent thereof, such as a nucleic acid or a cell.

A biological sample in a sample holder (e.g., microcentrifuge tube) that contains a mixture of desired biological particles or macromolecular constituents thereof (e.g., live cells) and undesired biological particles or macromolecular constituents thereof (e.g., dead cells, cell debris, or RNA) can be mixed with magnetic particles that trap the undesired biological particles or macromolecular constituents thereof (FIG. 5). The sample can then be applied to a system as described herein, and the magnetically labeled particles or macromolecular constituents thereof and non-magnetic particles or macromolecular constituents thereof can be separated from each other. In one embodiment, the desired particles or macromolecular constituents thereof, which are non-magnetically labeled, are captured in the flow through, whereas the magnetically labeled particles or macromolecular constituents thereof remain trapped near the magnetic features.

The sorting of particles may be used to enrich a mixture of particles for a desired species before formation of droplets. For example, the sorting may be used to enrich a mixture of cells, nuclei, or particulate components thereof for a desired species of cell (e.g., type of cell) or particulate component thereof (e.g., organelles, such as nuclei or mitochondria). The methods described herein may further include producing droplets containing the particles. By sorting the particles before producing the droplets, a larger fraction of the droplets will contain the desired species and/or number of particles within the droplet, and a reduced fraction of droplets will contain undesired species and/or number of droplets.

In some embodiments, the methods of separation allow a user to produce a population of particles having desired characteristics. For example, in some embodiments, following magnetic separation and incorporation into droplets, the method generates populations of droplets or particles that include a suitable fraction of desired droplets or particles (e.g., from 50% to 100%, from 60% to 100%, from 70% to 100%, from 80% to 100%, from 90% to 100%, or from 95% to 100% of droplets). In some embodiments, at least 10% e.g., at least 20%, 30%, 40%, 50%, 60%, 70%, 80%, 85%, 90%, 95%, 97%, 99%, or 100%, of the droplets or particles are usable for a desired purpose.

A variety of applications require the evaluation of the presence and quantification of different biological particle or organism types within a population of biological particles, including, for example, microbiome analysis and characterization, environmental testing, food safety testing, epidemiological analysis, e.g., in tracing contamination or the like.

Devices, systems, compositions, and methods of the present disclosure may be used for various applications, such as, for example, processing a single analyte (e.g., bioanalytes, e.g., RNA, DNA, or protein) or multiple analytes (e.g., bioanalytes, e.g., DNA and RNA, DNA and protein, RNA and protein, or RNA, DNA and protein) from a single cell or nucleus. For example, a biological particle (e.g., a cell, a nucleus, or virus) can be formed in a droplet, and one or more analytes (e.g., bioanalytes) from the biological particle (e.g., cell or nucleus) can be modified or detected (e.g., bound, labeled, or otherwise modified by an analyte moiety) for subsequent processing. The multiple analytes may be from the single cell or nucleus. This process may enable, for example, proteomic, transcriptomic, and/or genomic analysis of the cell/nucleus or population thereof (e.g., simultaneous proteomic, transcriptomic, and/or genomic analysis of the cell/nucleus or population thereof).

Methods of modifying analytes include providing a plurality of particles (e.g., beads) in a liquid carrier (e.g., an aqueous carrier); providing a sample containing an analyte (e.g., as part of a cell, nucleus, or component or product thereof) in a sample liquid; and using the device to combine the liquids and form an analyte droplet containing one or more particles and one or more analytes (e.g., as part of one or more cells, nuclei, or components or products thereof). Such sequestration of one or more particles with analyte (e.g., bioanalyte associated with a cell or a nucleus) in a droplet enables labeling of discrete portions of large, heterologous samples (e.g., single cells or nuclei within a heterologous population). Once labeled or otherwise modified, droplets or particles can be subsequently sorted or combined (e.g., by breaking an emulsion), and the resulting liquid can be analyzed to determine a variety of properties associated with each of numerous single cells or nuclei.

The invention also provides methods of single-cell (or single-nucleus) nucleic acid sequencing, in which a heterologous population of cells/nuclei can be characterized by their individual gene expression, e.g., relative to other cells/nuclei of the population. Methods of barcoding cells/nuclei discussed above and known in the art can be part of the methods of single-cell (or single nucleus) nucleic acid sequencing provided herein. After barcoding, nucleic acid transcripts that have been barcoded are sequenced, and sequences can be processed, analyzed, and stored according to known methods. In some embodiments, these methods enable the generation of a genome library containing gene expression data for any single cell or nucleus within a heterologous population.

EXAMPLES

The following examples describe devices and methods for magnetic separation.

Example 1

Figure 2:
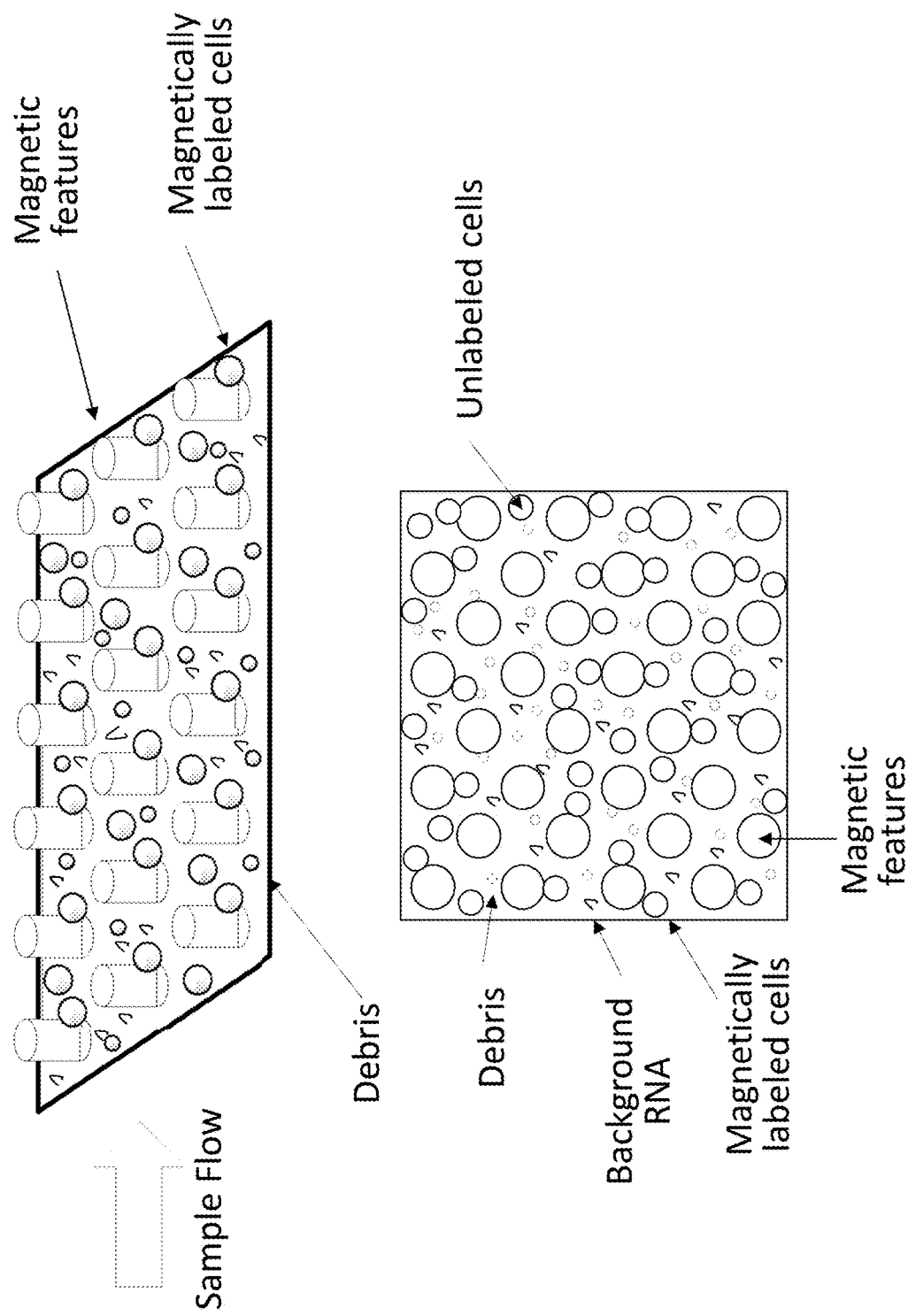
FIG. 2 is a schematic drawing of a system as described herein in which a sample with a plurality of magnetically labeled and unlabeled components pass through the flow module.

FIG. 1 is a schematic drawing of a system with a flow module (top) and a magnetic module (bottom). The flow module includes a sorting region having an inlet and an outlet and a plurality of voids around which particles and fluid can flow. The magnetic module includes a plurality of magnetic features (e.g., pillars) that mate with the plurality of voids and exert a magnetic gradient on magnetic particles that in the flow module. The magnetic module and flow module are separable. The two modules are integrated to form a system for magnetic separation, whereas the two modules can be separated to remove or reduce the magnetic gradient on magnetic particles in the flow module FIG. 2 is a schematic drawing of a system as described herein in which a sample with a plurality of magnetically labeled and unlabeled components pass through the flow module, e.g., from left to right. Shown on top is a perspective view of the magnetic module with a plurality of magnetic features. Shown on the bottom is a top view of the magnetic module mated with the flow module. The sample contains a liquid with a mixture of magnetically labeled and unlabeled components. The magnetically labeled particles are attracted by the magnetic force produced by the magnetic features and are immobilized adjacent the voids, whereas the unlabeled components are not attracted by the magnetic force and are not immobilized adjacent the voids.

Figure 3:
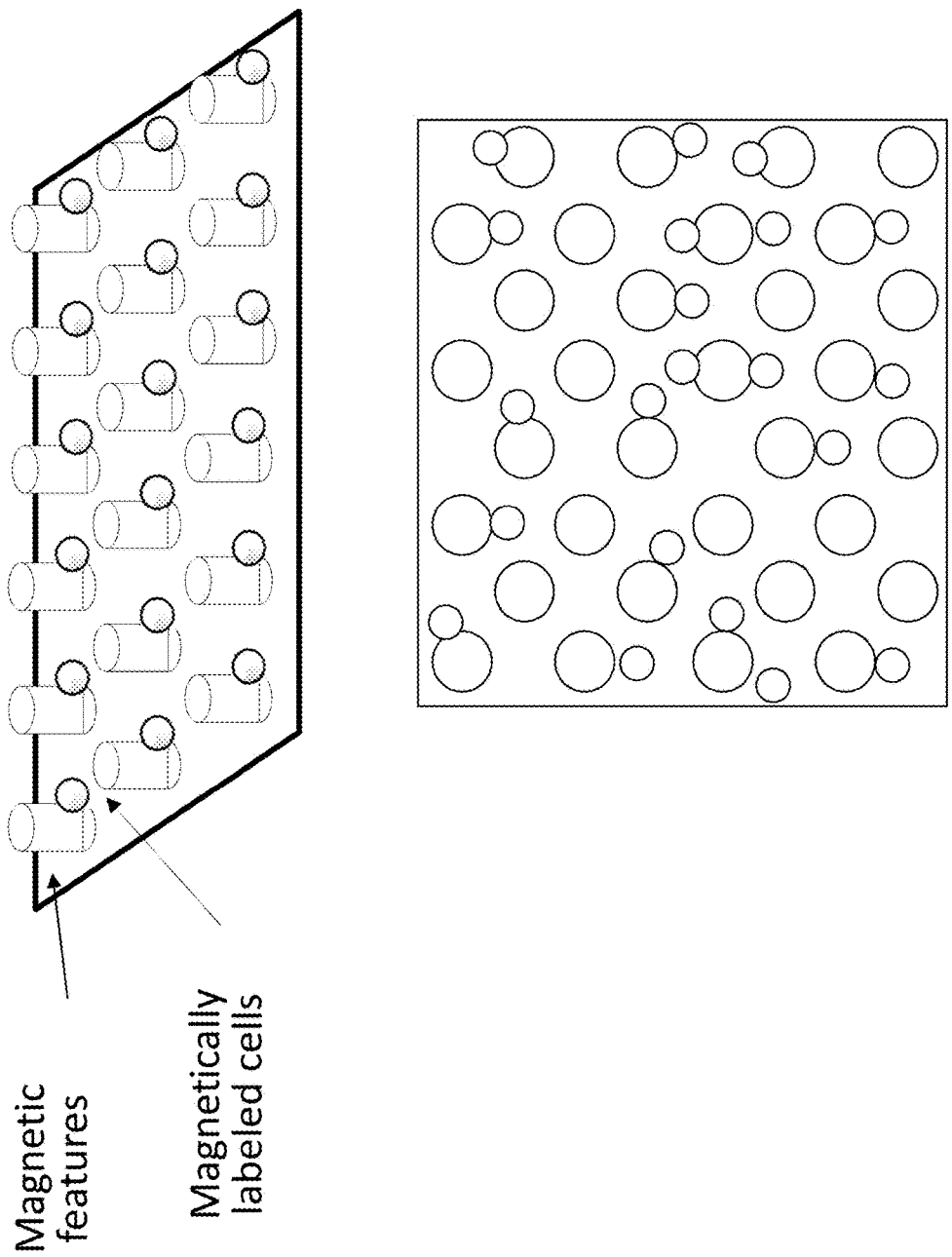
FIG. 3 is a schematic drawing of a system as described herein in which the magnetically labeled particles are immobilized adjacent the voids

Once the magnetic particles move towards the magnetic features, the liquid can be removed, e.g., by flowing a liquid through the flow module, thereby washing away undesired components. FIG. 3 shows magnetically labeled particles that are immobilized adjacent the voids. The unlabeled components (e.g., cells, debris, background RNA) have been washed away, and only the labeled cells remain. The magnetic module can be removed to allow the magnetic particles to be resuspended in a liquid that flows through the flow module to produce a sample enriched in the magnetic particles. The magnetic separation can be repeated multiple times to continuously enrich the sample for the magnetic particles.

Figure 4:
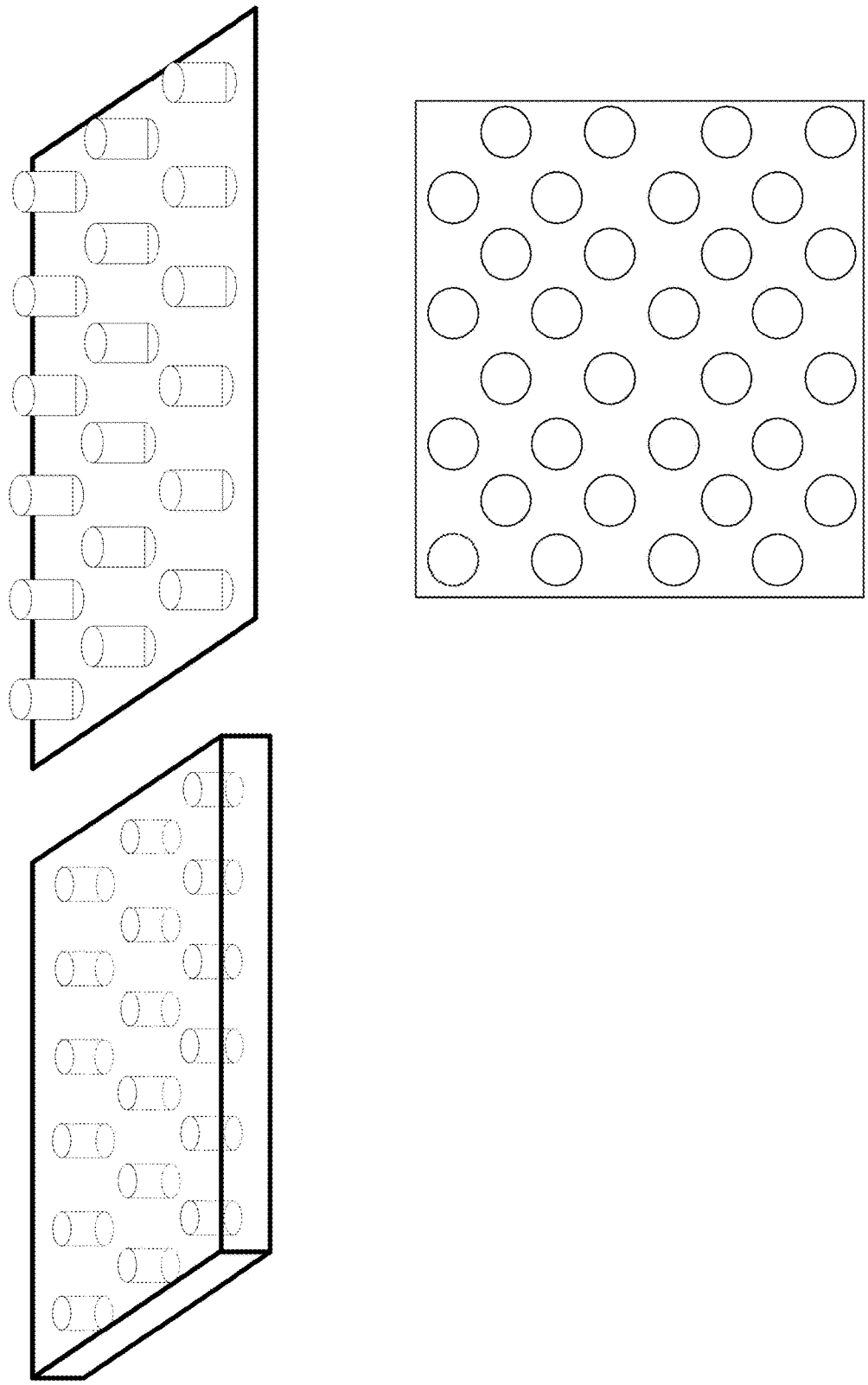
FIG. 4 is a schematic drawing of a system in which the magnetically labeled particles (e.g., cells) have been eluted from the magnetic features.

FIG. 4 is a schematic drawing of a system in which the magnetically labeled particles (e.g., cells) have been eluted from the magnetic features. The magnetic module is removed from the flow module, and the labeled cells are eluted into a collection region (e.g., a tube) by flowing a liquid through the flow module. The top panel shows a perspective view of the separable flow module and magnetic module, and the bottom panel shows a top view.

Example 2

FIG. 5 is a schematic drawing showing a sample preparation step that can be used before magnetophoresis using a system as described herein. A biological sample in a sample holder (e.g., microcentrifuge tube) that contains a mixture of desired biological particles (e.g., live cells or intact nuclei) and undesired biological particles and macromolecular constituents thereof (e.g., dead cells, cell debris, or RNA) is mixed with magnetic particles that trap the undesired biological particles or macromolecular constituents thereof. The top panel shows magnetic beads capturing RNA and cellular debris, and the bottom panel shows magnetic beads capturing RNA. In the top panel, the desired biological particles (e.g., live cells or intact nuclei) remain free in solution, whereas the undesired particles or macromolecular constituents thereof (e.g., dead cells and RNA) are trapped by the magnetic particles. In the bottom panel, the live cells and dead cells remain free in solution, whereas the RNA is trapped by the magnetic particles. The sample can then be applied to a system as described herein (e.g., as in Example 1), and the magnetically labeled particles and non-magnetically labeled particles can be separated from each other. In one embodiment, the desired particles, which are non-magnetically labeled, are captured in the flow through, whereas the magnetically labeled particles remain trapped near the magnetic features.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

Other embodiments are in the claims.

The invention claimed is:

1. A method for magnetic separation comprising:
   (a) providing a system for magnetic separation comprising:
      (i) a flow module comprising a sorting region having an inlet and an outlet and comprising a plurality of voids around which particles and fluid can flow, wherein the plurality of voids is arranged in a two-dimensional array, and wherein each of the plurality of voids has a height that extends across the sorting region of the flow module; and
      (ii) a magnetic module comprising a plurality of magnetic features that mate with the plurality of voids, wherein the magnetic and flow modules are separable; and
   a sample comprising magnetic particles suspended in a liquid; and
   (b) allowing the sample to enter the sorting region and to flow around the plurality of voids, wherein the magnetic particles are immobilized adjacent the plurality of voids in the sorting region.

2. The method of claim 1, further comprising washing the magnetic particles after step (b).

3. The method of claim 1, further comprising eluting the magnetic particles after step (b).

4. The method of claim 3, wherein the eluting of the magnetic particles comprises removing the magnetic module from the flow module.

5. The method of claim 3, wherein the eluting of the magnetic particles comprises resuspending the magnetic particles in a second liquid.

6. The method of claim 1, wherein the magnetic particles are attached to a biological particle or a macromolecular constituent thereof.

7. The method of claim 6, wherein the biological particle is a cell.

8. The method of claim 1, wherein the magnetic features comprise an average width of from about 1 μm to about 10 mm.

9. The method of claim 1, wherein the magnetic features are spaced apart at an average distance of from about 1 nm to about 100 μm.

10. The system of claim 9, wherein the magnetic features are spaced apart at an average distance of from about 10 nm to about 1 μm.

11. The system of claim 9, wherein the magnetic features are spaced apart at an average distance of from about 5 μm to about 10 μm.

12. The system of claim 9, wherein the magnetic features are spaced apart at an average distance of from about 10 μm to about 50 μm.

13. The method of claim 3, wherein the flow module further comprises a collection region in fluid communication with the outlet, and the magnetic particles are eluted into the collection region.

14. The method of claim 1, wherein each of the plurality of voids comprises a wall having a thickness of 10 μm to about 10 mm that separates the magnetic features from particles and fluid in the sorting region.

15. The method of claim 1, wherein the magnetic features are magnetizable, and the system further comprises a magnet that exerts a magnetic force on the magnetic features, thereby immobilizing the magnetic particles adjacent the plurality of voids in the sorting region.

16. The method of claim 1, wherein the magnetic features comprise a ferromagnetic or paramagnetic material.

17. The method of claim 1, wherein the flow module comprises plastic, glass, or silicon.

18. The method of claim 1, wherein each of the plurality of voids has a cylindrical or polygonal cross-section.

19. The method of claim 18, wherein the cylindrical or polygonal cross-section is triangular or rectangular.

* * * * *